US012698513B2

(12) United States Patent
Baram et al.

(10) Patent No.: US 12,698,513 B2
(45) Date of Patent: Aug. 4, 2026

(54) CRISPR COMPOSITIONS AND METHODS FOR PROMOTING GENE EDITING OF RIBOSOMAL PROTEIN S19 (RPS19) GENE

(71) Applicant: EmendoBio Inc., Wilmington, DE (US)

(72) Inventors: David Baram, Tel Aviv (IL); Lior Izhar, Tel Aviv (IL); Asael Herman, Ness-Ziona (IL); Rafi Emmanuel, Ramla (IL); Michal Golan Mashiach, Ness-Ziona (IL); Joseph Georgeson, Rehovot (IL)

(73) Assignee: EmendoBio Inc., Wilmington, DE (US)

( * ) Notice: Subject to any disclaimer, the term of this patent is extended or adjusted under 35 U.S.C. 154(b) by 1187 days.

(21) Appl. No.: 17/428,880

(22) PCT Filed: Feb. 4, 2020

(86) PCT No.: PCT/US2020/016643
§ 371 (c)(1),
(2) Date: Aug. 5, 2021

(87) PCT Pub. No.: WO2020/163379
PCT Pub. Date: Aug. 13, 2020

(65) Prior Publication Data
US 2022/0098621 A1    Mar. 31, 2022

Related U.S. Application Data

(60) Provisional application No. 62/861,183, filed on Jun. 13, 2019, provisional application No. 62/801,603, filed on Feb. 5, 2019.

(51) Int. Cl.
| | |
|---|---|
| *A61P 7/06* | (2006.01) |
| *A61K 31/7105* | (2006.01) |
| *A61K 35/28* | (2015.01) |
| *C12N 5/0789* | (2010.01) |
| *C12N 9/22* | (2006.01) |
| *C12N 15/11* | (2006.01) |
| *C12N 15/90* | (2006.01) |

(52) U.S. Cl.
CPC ........ *C12N 15/907* (2013.01); *A61K 31/7105* (2013.01); *A61K 35/28* (2013.01); *A61P 7/06* (2018.01); *C12N 5/0647* (2013.01); *C12N 9/22* (2013.01); *C12N 15/11* (2013.01); *C12N 2310/20* (2017.05); *C12N 2501/125* (2013.01); *C12N 2501/22* (2013.01); *C12N 2501/2303* (2013.01); *C12N 2510/00* (2013.01); *C12N 2800/80* (2013.01)

(58) Field of Classification Search
None
See application file for complete search history.

(56) References Cited

U.S. PATENT DOCUMENTS

2014/0170753 A1* 6/2014 Zhang ................... C12N 15/63
435/320.1

FOREIGN PATENT DOCUMENTS

WO    WO-2017191187 A2 * 11/2017    ......... G01N 33/5026

OTHER PUBLICATIONS

Clancy, S. (2008) RNA Functions. Nature Education 1(1):102 (Year: 2008).*
Bernat et al. RNA Structures as Mediators of Neurological Diseases and as Drug Targets. Neuron. Jul. 1, 2015;87(1):28-46. (Year: 2015).*
Nowak et al. Guide RNA engineering for versatile Cas9 functionality. Nucleic Acids Res. Nov. 16, 2016;44(20):9555-9564. Epub Oct. 12, 2016. (Year: 2016).*
International Preliminary Report on Patentability issued Aug. 10, 2021 including Written Opinion of the International Searching Authority issued Jul. 5, 2020, in connection with PCT International Application No. PCT/US2020/016551.
International Search Report issued Jul. 17, 2020 in connection with PCT International Application No. PCT/US2020/016643.
Written Opinion (form PCT/ISA/237) issued Jul. 17, 2020 in connection with PCT International Application No. PCT/US2020/016643.
Aguirre, A. J. "Genomic Copy Number Dictates a Gene-Independent Cell Response to CRISPR/Cas9 Targeting." Cancer Discovery, vol. 6, No. 8, Jun. 3, 2016, pp. 914-929 and Supplementary data.
Anonymous: "Diamond Blackfan Anemia Foundation Hosts 14th DBA International Consensus Conference." 2016.
Anonymous: "NM_001022. 3 (RPS19):c.—339T>C." ClinVar Database, Jun. 14, 2016.
Aspesi, A. et al. "Emerging Therapeutic Approaches for Diamond Blackfan Anemia." Current Gene Therapy, vol. 18, No. 6, Dec. 12, 2018, pp. 327-335.
Campagnoli, M. F. "RPS19 Mutations in Patients With Diamond-Blackfan Anemia." Human Mutation, vol. 29, No. 7, Apr. 15, 2008, pp. 911-920.
Da Costa, L. "Molecular approaches to diagnose Diamond-Blackfan anemia: The EuroDBA experience." European Journal of Medical Genetics, vol. 61, No. 11, Oct. 26, 2017, pp. 664-673.
Doench, J. G. et al. "Optimized sgRNA design to maximize activity and minimize off-target effects of CRISPR-Cas9." Nature Biotechnology, vol. 34, No. 2, Jan. 18, 2016, pp. 184-191 and Tables S21-S22.

(Continued)

*Primary Examiner* — Valarie E Bertoglio
*Assistant Examiner* — Briana N Ebbinghaus
(74) *Attorney, Agent, or Firm* — Faegre Drinker Biddle & Reath LLP

(57) ABSTRACT

Isolated guide RNA (gRNA) molecules comprising CRISPR (crRNA) molecules that target the 19:41869823_T_C mutation of a Ribosomal Protein S19 (RPS19) allele.

10 Claims, 3 Drawing Sheets

Specification includes a Sequence Listing.

(56) References Cited

OTHER PUBLICATIONS

Westin, E. et al. "Correction of Diamond-Blackfan Induced Pluripotent Stem Cells via CRISPR." Abstracts of "Molecules for Minions: Southeastern Pediatric Research Innovation Conference," Jun. 22, 2016, Atlanta, p. 17.

Westin, E. et al. "Crispr Modification of Induced Pluripotent StemDerived from Diamond-Blackfan Anemia Fibroblasts." Blood, vol. 124, No. 21, Dec. 6, 2014.

* cited by examiner

CRISPR COMPOSITIONS AND METHODS FOR PROMOTING GENE EDITING OF RIBOSOMAL PROTEIN S19 (RPS19) GENE

CROSS-REFERENCE TO RELATED APPLICATIONS

This application is a $371 national stage of PCT International Application No, PCT/US2020/016643, filed Feb. 4, 2020, claiming the benefit of U.S. Provisional Applications Nos. 62/861,183, filed Jun. 13, 2019, and 62/801,603, filed Feb. 5, 2019, the contents of each of which are hereby incorporated by reference into the application.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide and/or amino acid sequences which are present in the file named "210805_90838-A-PCT-US_Sequence_Listing_LMO.txt," which is 3740 kilobytes in size, and which was created Jul. 21, 2021 in the IBM-PC machine format, having an operating system compatibility with MS-Windows, which is contained in the text file filed Aug. 5, 2021 as part of this application.

BACKGROUND OF INVENTION

There are several classes of DNA variation in the human genome, including insertions and deletions, differences in the copy number of repeated sequences, and single nucleotide polymorphisms (SNPs). A SNP is a DNA sequence variation occurring when a single nucleotide (adenine (A), thymine (T), cytosine (C), or guanine (G)) in the genome differs between human subjects or paired chromosomes in an individual. Over the years, the different types of DNA variations have been the focus of the research community either as markers in studies to pinpoint traits or disease causation or as potential causes of genetic disorders.

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Additional examples include dominant negative mutations, which have a gene product that acts antagonistically to the wild-type allele. Other examples include haploinsufficiency, that may be caused by a loss of function mutation in which a reduced dosage of a normal gene product is not sufficient to produce the normal phenotype.

Diamond Blackfan Anemia

Diamond Blackfan anemia (DBA) primarily affects the bone marrow, which produces new blood cells. People with this condition often also have physical abnormalities affecting various parts of the body. DBA patients were found to possess mutations in the ribosomal protein genes. Genes susceptible for the mutations in DBA patients include RPL3, RPL5, RPL11, RPL15, RPL26, RPL31, RPL35A, RPL36, RPS7, RPS10, RPS14, RPS17, RPS19, RPS24, RPS26 and RPS29 gene. A variety of mutations in RPS19 gene including whole gene deletions, translocations, truncating mutations (nonsense or frameshift) or missense mutations were identified in DBA patients. The RPS19 gene encodes a ribosomal protein that is a component of the 40S subunit. The protein belongs to the S19E family of ribosomal proteins. The RPS19 gene mutations that cause Diamond-Blackfan anemia are believed to cause problems with ribosomal function. Studies indicate that a shortage of functioning ribosomes may increase apoptosis of blood-forming cells in the bone marrow, resulting in a low number of red blood cells (anemia).

SUMMARY OF THE INVENTION

Disclosed is an approach for repairing an allele bearing a disease-associated mutation ("mutant allele") by utilizing an RNA guided DNA nuclease to edit/correct/modify the nucleic acid sequence of the mutant allele such as to express a functional protein. In some embodiments, the approach is for repairing an allele bearing a dominant disease-associated mutation. The method of the enclosed invention may utilize allele-specific or non-discriminatory guide sequences to target and correct a disease-associated mutation.

According to some embodiments, the present disclosure provides a method for differentiating between the mutant allele and the wild type allele of a gene in order to edit only the mutant allele. In some embodiments, the differentiation is based on designing a guide RNA that targets a difference in sequence between the mutant allele and the functional allele. Such difference may be due to a heterozygous SNP, or a heterozygous disease-causing mutation.

According to some embodiments, the method utilizes at least one naturally occurring nucleotide difference or polymorphism (e.g., single nucleotide polymorphism (SNP)) between two alleles of a gene, to target an allele of a gene bearing a mutation causing a disease phenotype and a particular sequence in the SNP position. For example, a mutant allele in a cell can be specifically targeted based on a SNP and/or mutation sequence relative to another functional or wild-type allele in a cell which lacks the SNP and/or mutation. In some embodiments, a particular sequence in the SNP position is utilized for distinguishing/discriminating between two alleles of a gene, one allele bearing a mutation such that it encodes a mutated protein causing a disease phenotype ("mutant allele"), and the other allele encoding for a functional/normal/wild type protein ("functional allele"), such as to target the mutant allele bearing both a particular sequence in the SNP position and a disease associated mutation. In some embodiments, the disease-associated mutation is targeted. In some embodiments, the method further comprises the step of allele cleavage by a CRISPR nuclease. The allele cleavage is selected from the group consisting of a double strand break (DSB) and a single strand break. In some embodiments, the method further comprises the step of correction of the allele such that the corrected allele results in an expression of a functional RPS19 protein. In some embodiments, the correction is performed by homology directed repair (HDR). In some embodiments, the allele is altered such that it no longer possesses dominant negative properties.

According to embodiments of the present invention, there is provided an RNA molecule comprising a guide sequence portion having 17-25 nucleotides in the sequence of 17-25 contiguous nucleotides set forth in any one of SEQ ID NOs: 1-20465.

According to some embodiments of the present invention, there is provided a composition comprising an RNA molecule comprising a guide sequence portion having 17-25 contiguous nucleotides containing nucleotides in the sequence set forth in any one of SEQ ID NOs 1-20465 and a CRISPR nuclease. In some embodiments, the composition further comprises a nucleic acid template for homology-directed repair, alteration, or replacement of a target sequence of an allele comprising the disease-associated mutation.

According to some embodiments of the present invention, there is provided a method for repairing or correcting a mutant RPS19 allele in a cell, the method comprising delivering to the cell a composition comprising an RNA molecule comprising a guide sequence portion having 17-25 contiguous nucleotides containing nucleotides in the sequence set forth in any one of SEQ ID NOs 1-20465 and a CRISPR nuclease. In some embodiments, a nucleic acid template is further provided to the cell for homology-directed repair, alteration, or replacement of a target sequence of the mutant RPS19 allele. In some embodiments, an endogenous template is utilized to repair, alter, or replace the target sequence of the mutant RPS19 allele. In some embodiments, non-templated repair alters the RPS19 allele.

According to some embodiments of the present invention, there is provided a method for treating, preventing or ameliorating a condition in a subject having Diamond-Blackfan anemia (DBA), the method comprising delivering to the subject a composition comprising an RNA molecule comprising a guide sequence portion having 17-25 contiguous nucleotides containing nucleotides in the sequence set forth in any one of SEQ ID NOs 1-20465 and a CRISPR nuclease. In some embodiments, a nucleic acid template is further provided to the cell for homology-directed repair, alteration, or replacement of a target DNA sequence comprising the pathogenic mutation. In some embodiments, an endogenous template is utilized to repair, alter, or replace the target sequence of the mutant RPS19 allele. In some embodiments, non-templated repair alters the RPS19 allele.

In some embodiments, the method is performed ex-vivo and the cell is provided or explanted from an individual patient. In some embodiments, the method further comprises the step of introducing the resulting cell with the corrected, repaired, or modified mutant RPS19 allele, into the individual patient (e.g. autologous transplantation).

According to some embodiments of the present invention, there is provided use of a composition comprising an RNA molecule comprising a guide sequence portion having 17-25 contiguous nucleotides containing nucleotides in the sequence set forth in any one of SEQ ID NOs 1-20465 and a CRISPR nuclease for repairing/correcting/editing a mutant RPS19 allele in a cell, comprising delivering to the cell the composition comprising an RNA molecule comprising a guide sequence portion having 17-25 contiguous nucleotides containing nucleotides in the sequence set forth in any one of SEQ ID NOs 1-20465 and a CRISPR nuclease.

According to embodiments of the present invention, there is provided a medicament comprising an RNA molecule comprising a guide sequence portion having 17-25 contiguous nucleotides containing nucleotides in the sequence set forth in any one of SEQ ID NOs 1-20465 and a CRISPR nuclease for use in inactivating repairing/correcting/editing a mutant RPS19 allele in a cell, wherein the medicament is administered by delivering to the cell the composition comprising an RNA molecule comprising a guide sequence portion having 17-25 contiguous nucleotides containing nucleotides in the sequence set forth in any one of SEQ ID NOs 1-20465 and a CRISPR nuclease. In some embodiments, the medicament further comprises a nucleic acid template.

According to some embodiments of the present invention, there is provided use of a composition comprising an RNA molecule comprising a guide sequence portion having 17-25 contiguous nucleotides containing nucleotides in the sequence set forth in any one of SEQ ID NOs 1-20465 and a CRISPR nuclease for treating ameliorating or preventing DBA, comprising delivering to cells of a subject having or at risk of having DBA, the composition comprising an RNA molecule comprising a guide sequence portion having 17-25 contiguous nucleotides containing nucleotides in the sequence set forth in any one of SEQ ID NOs 1-20465 and a CRISPR nuclease.

According to some embodiments of the present invention, there is provided a medicament comprising the composition comprising an RNA molecule comprising a guide sequence portion having 17-25 contiguous nucleotides containing nucleotides in the sequence set forth in any one of SEQ ID NOs 1-20465 and a CRISPR nuclease for use in treating ameliorating or preventing DBA, wherein the medicament is administered by delivering to a subject having or at risk of having DBA the composition comprising an RNA molecule comprising a guide sequence portion having 17-25 contiguous nucleotides containing nucleotides in the sequence set forth in any one of SEQ ID NOs 1-20465 and a CRISPR nuclease.

According to some embodiments of the present invention, there is provided a kit for correcting/repairing a mutant RPS19 allele in a cell, comprising an RNA molecule comprising a guide sequence portion having 17-25 contiguous nucleotides containing nucleotides in the sequence set forth in any one of SEQ ID NOs 1-20465, a CRISPR nuclease, and optionally a tracrRNA molecule; and instructions for delivering the RNA molecule; CRISPR nuclease, and/or the tracrRNA to the cell. In some embodiment, the delivery is performed ex-vivo. In some embodiments, the delivery is performed within a subject's body. In some embodiments, the cells are HSC cell originated from the subject.

According to some embodiments of the present invention, there is provided a kit for treating DBA in a subject, comprising an RNA molecule comprising a guide sequence portion having 17-25 contiguous nucleotides containing nucleotides in the sequence set forth in any one of SEQ ID NOs 1-20465, a CRISPR nuclease, and optionally a tracrRNA molecule; and instructions for delivering the RNA molecule; CRISPR nuclease, and optionally the tracrRNA to a subject having or at risk of having DBA. According to some embodiments of the present invention, there is provided a kit for treating DBA in a subject, comprising an RNA molecule comprising a guide sequence portion having 17-25 contiguous nucleotides containing nucleotides in the sequence set forth in any one of SEQ ID NOs 1-20465, a CRISPR nuclease, and optionally a tracrRNA molecule; and instructions for delivering the RNA molecule; CRISPR nuclease, and optionally the tracrRNA to cells of the subject having or at risk of having DBA. In some embodiments, the cells are HSC cells obtained from the subject and the delivery is ex-vivo.

The present invention also provides a method for repairing, correcting, or modifying a gene bearing a dominant disease-associated mutation. The method utilizes at least one guide sequence for targeting a CRISPR nuclease to a target sequence in a non-coding region of a gene bearing a mutation causing a disease phenotype. In some embodiments, the targeting is to a non-coding region of each of two alleles of the gene, one allele bearing a mutation such that it encodes a mutated protein causing a disease phenotype ("mutant allele"), and the other allele encoding for a functional/ normal/wild type protein ("functional allele"). In some embodiments, the target sequence is in a distance of up to 1000, 900, 800, 700, 600, 500, 400, 300, 200 base pairs from the edges of an exon bearing the mutation causing the disease phenotype. Each possibility represents a separate embodiment. In some embodiments, the method further comprises the step of allele cleavage by a CRISPR nuclease. The allele cleavage is selected from the group consisting of: a double strand break (DSB) and a single strand break. In some embodiments, the method further comprises the step of correction of the allele such that the corrected allele results in an expression of a functional RPS19 protein. In some embodiments, the correction is performed by homology directed repair (HDR).

The present invention provides for a method for modifying in a cell a mutant allele of the Ribosomal Protein S19 gene (RPS19 gene) having a mutation associated with Diamond Blackfan anemia (DBA), the method comprising introducing to the cell a composition comprising:

a CRISPR nuclease or a sequence encoding the CRISPR nuclease; and a first RNA molecule comprising a guide sequence portion having 17-25 nucleotides or a nucleotide sequence encoding the same, wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA.

The present invention also provides for a modified cell obtained by any of the methods of the present invention.

The present invention provides for a composition comprising the modified cells of the present invention and a pharmaceutically acceptable carrier.

The present invention also provides for an in vitro or ex vivo method of preparing the compositions of the present invention, comprising mixing the cells with the pharmaceutically acceptable carrier.

The present invention provides for a method of preparing in vitro or ex vivo a composition comprising modified cells, the method comprising:

a) isolating HSPCs from cells obtained from a subject with an RPS19 gene mutation related to DBA and/or suffering from DBA, and obtaining the cell from the subject;

b) introducing to the cells of step (a) a composition comprising:

a CRISPR nuclease or a sequence encoding the CRISPR nuclease; and a first RNA molecule comprising a guide sequence portion having 17-25 nucleotides, wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA, optionally, introducing to the cells a donor DNA template for homology directed repair (HDR), alteration, or replacement of a target sequence of the RPS19 allele so as to modify the mutant allele of the RPS19 gene in one or more cells thereby obtaining modified cells; optionally c) culture expanding the modified cells of step (b), wherein the modified cells are capable of engraftment and giving rise to progeny cells after engraftment.

The present invention provides for use of a composition prepared in vitro by a method comprising:

a) isolating HSPCs from cells obtained from a subject with an RPS19 gene mutation related to DBA and/or suffering from DBA, and obtaining the cell from the subject;

b) introducing to the cells of step (a) a composition comprising:

a CRISPR nuclease or a sequence encoding the CRISPR nuclease; and a first RNA molecule comprising a guide sequence portion having 17-25 nucleotides, wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA, optionally, introducing to the cells a donor DNA template for homology directed repair (HDR), alteration, or replacement of a target sequence of the RPS19 allele so as to modify the mutant allele of the RPS19 gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c) for treating the DBA in the subject.

The present invention provides for a method of treating a subject afflicted with DBA, comprising administration of a therapeutically effective amount of the modified cells, the compositions, or the compositions prepared by the methods of the present invention.

The present invention provides for a method for treating DBA in a subject with an RPS19 gene mutation relating to DBA in need thereof, the method comprising:

a) isolating HSPCs from cells obtained from the subject;

b) introducing to the cells of step (a) a composition comprising:

a CRISPR nuclease or a sequence encoding the CRISPR nuclease; and a first RNA molecule comprising a guide sequence portion having 17-25 nucleotides, wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA, optionally, introducing to the cells a donor DNA template for homology directed repair (HDR), alteration, or replacement of a target sequence of the RPS19 allele so as to modify the mutant allele of the RPS19 gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c)

thereby treating the DBA in the subject.

The present invention provides for a method for treating DBA in a subject with an RPS19 gene mutation relating to DBA in need thereof, the method comprising administering to the subject autologous modified cells or progeny of autologous modified cells, wherein the autologous modified cells are modified so as to have a correction of the mutant allele of the RPS19 gene from the mutant phenotype to a non-mutant phenotype, wherein said double strand break results from introduction to the cells of a composition comprising a CRISPR nuclease or sequence encoding the CRISPR nuclease and a first RNA molecule wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA, thereby treating the DBA in the subject.

The present invention provides for an RNA molecule comprising a guide sequence portion having 17-25 contiguous nucleotides containing nucleotides in the sequence set forth in any one of SEQ ID NOs 1-20465.

The present invention provides for a composition comprising the RNA molecules of the present invention and a donor DNA template for homology directed repair (HDR), alteration, or replacement of a target sequence of the RPS19 allele.

The present invention provides for a method for modifying in a cell a mutant allele of the RPS19 gene, the method comprising delivering to the cell the RNA molecules of the present invention or the compositions of the present invention.

The present invention provides for a method for treating DBA, the method comprising delivering to a subject having DBA the RNA molecules of the present invention or the compositions of present invention, or cells modified by the RNA molecules of the present invention or the compositions of the present invention.

The present invention provides for use of the RNA molecules of the present invention, the compositions of the present invention, or the composition prepared by the methods of the present invention, for modifying in a cell a mutant RPS19 allele.

The present invention provides for a medicament comprising the RNA molecules of the present invention, the compositions of the present invention, or the composition prepared by the methods of the present invention for use in inactivating in a cell a mutant RPS19 allele, wherein the medicament is administered by delivering to the cell the RNA molecules of the present invention, the compositions of the present invention, or the composition prepared by the methods of the present invention.

The present invention provides for use of the methods of the present invention, the modified cells of the present invention, the compositions of the present invention, or the compositions prepared by the methods of the present invention, or the RNA molecules of the present invention for treating ameliorating or preventing DBA in to a subject having or at risk of having DBA.

The present invention provides for a medicament comprising the RNA molecules of the present invention, the compositions of the present invention, the compositions prepared by the methods of the present invention, or the modified cells of the present invention, for use in treating ameliorating or preventing DBA, wherein the medicament is administered by delivering to a subject having or at risk of having DBA the RNA molecules of the present invention, the compositions of the present invention, the compositions prepared by the methods of the present invention, or the modified cells of the present invention.

The present invention provides for a kit for inactivating a mutant RPS19 allele in a cell, comprising an RNA molecule of the present invention, a CRISPR nuclease or a sequence encoding the CRISPR nuclease, and/or a tracrRNA molecule or a sequence encoding the tracrRNA; and instructions for delivering the RNA molecule; CRISPR nuclease or a sequence encoding the CRISPR nuclease, and/or the tracrRNA molecule or a sequence encoding the tracrRNA to the cell to modify the mutant RPS19 allele in the cell.

The present invention provides for a kit for treating DBA in a subject, comprising an RNA molecule of the present invention, a CRISPR nuclease or a sequence encoding the CRISPR nuclease, and/or a tracrRNA molecule or a sequence encoding the tracrRNA; and instructions for delivering the RNA molecule; CRISPR nuclease or sequence encoding the CRISPR nuclease, and/or tracrRNA molecule or sequence encoding the tracrRNA to a subject having or at risk of having DBA so as to treat the DBA.

The present invention provides for a kit for inactivating a mutant RPS19 allele in a cell, comprising the compositions of the present invention, the compositions prepared by the methods of the present invention, or the modified cells of the present invention, and instructions for delivering the composition to the cell so as to modify the RPS19 gene in the cell.

The present invention provides for a kit for treating DBA in a subject, comprising the compositions of the present invention, the compositions prepared by the methods of the present invention, or the modified cells of the present invention, and instructions for delivering the compositions of the present inventions, the compositions prepared by the methods of the present invention, or the modified cells of the present invention, to a subject having or at risk of having DBA so as to treat DBA.

BRIEF DESCRIPTION OF THE DRAWINGS

FIG. 1A represents an allele specific editing approach based on targeting a nuclease (scissors accompanied by an arrow indicating the target site) to a pathogenic mutation (black box) in an exon (e.g. exon 4) of the RPS19 gene. FIG. 1B represents an allele specific editing approach based on targeting a nuclease (scissors accompanied by an arrow indicating the target site) to a heterozygous SNP (star). FIG. 1C represents a bi-allelic editing approach based on utilizing non-discriminatory guides to target a nuclease (scissors accompanied by an arrow indicating the target site) to both mutant and functional RPS19 alleles at non-coding regions within 250 basepairs of an edge of an exon bearing a pathogenic mutation position.

DETAILED DESCRIPTION

Figure 1A:
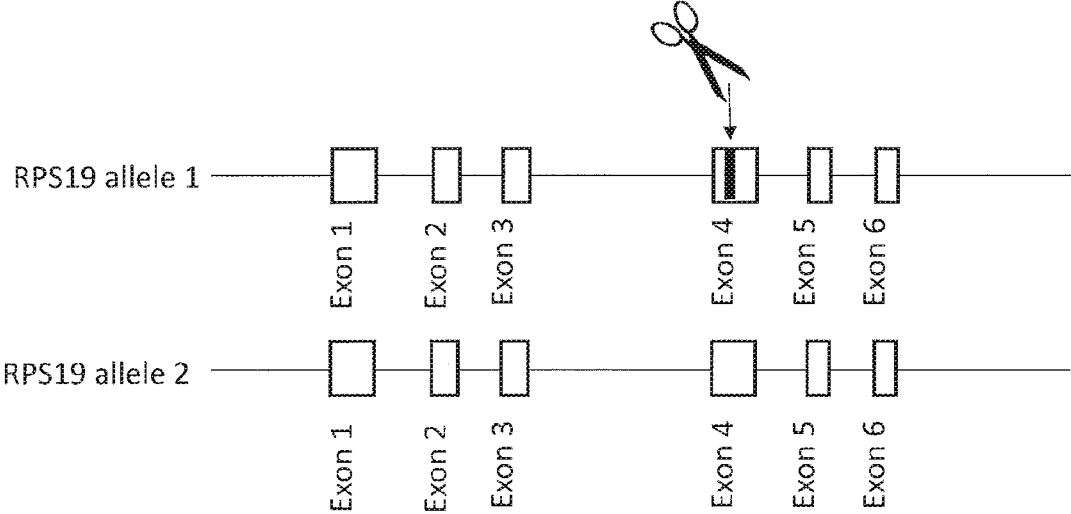
FIG. 1A-FIG. 1C: A schematic representation of the three editing strategies disclosed herein.
Figure 1B:
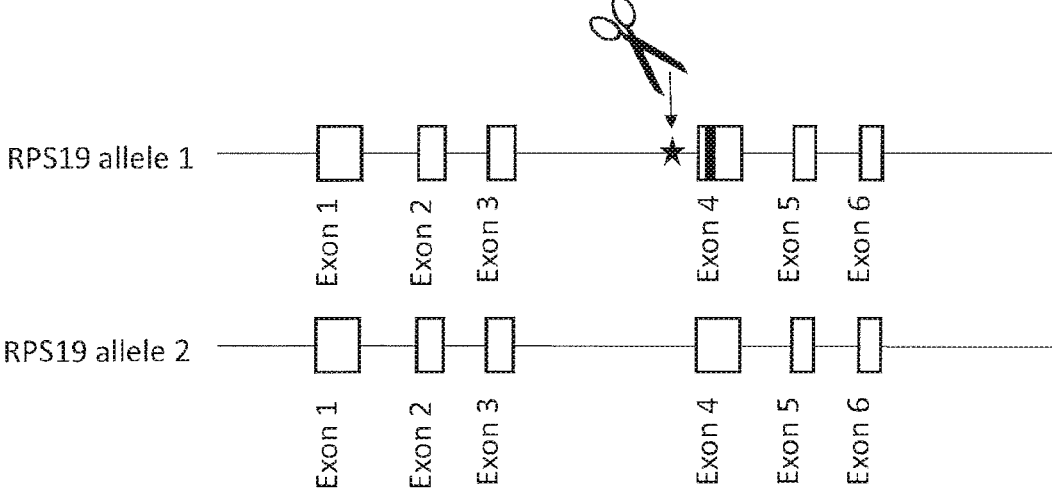
Figure 1C:
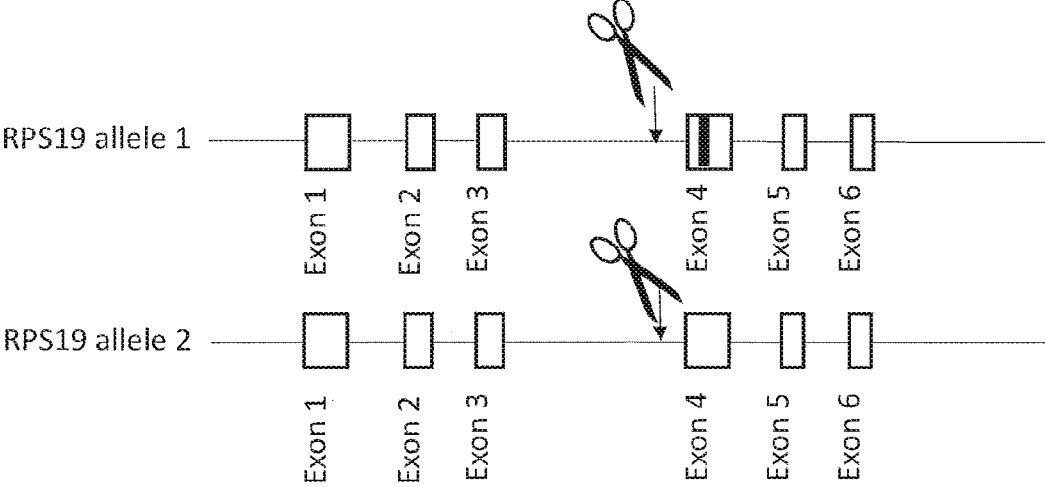

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, 24, or 25 nucleotides in length, or approximately 17-25, 17-24, 17-22, 17-21, 18-25, 18-24, 18-23, 18-22, 18-21, 19-25, 19-24, 19-23, 19-22, 19-21, 19-20, 20-22, 18-20, 20-21, 21-22, or 17-20 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

In embodiments of the present invention, an RNA molecule comprises a guide sequence portion having 17-25 contiguous nucleotides containing nucleotides in the sequence set forth in any one of SEQ ID NOs 1-20465. In some embodiments, the guide sequence portion have 17-25 contiguous nucleotides containing nucleotides in the sequence set forth in any one of SEQ ID NOs 1-20465. In some embodiments, the aforementioned guides are allele-specific. In some embodiments, the aforementioned guides target a SNP position. In some embodiments, the aforementioned guides target a pathogenic mutation. In some embodiments, the aforementioned guides target a non-coding region of each of the RPS19 alleles.

The term "targets" as used herein, refers to the guide sequence portion of the RNA molecule's preferential hybridization to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context of targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is affected by a complex of an RNA molecule and the CRISPR nuclease as a result of hybridization with the target sequence, i.e. on-target hybridization. The term "modified cells" may further encompass cells in which a repair or correction of a mutation was affected following the double strand break.

As used herein, "contiguous nucleotides" set forth in a SEQ ID NO refers to nucleotides in a sequence of nucleotides in the order set forth in the SEQ ID NO without any intervening nucleotides.

The RNA molecule and or the guide sequence portion of the RNA molecule may contain modified nucleotides. Exemplary modifications to nucleotides/polynucleotides may be synthetic and encompass polynucleotides which contain nucleotides comprising bases other than the naturally occurring adenine, cytosine, thymine, uracil, or guanine bases. Modifications to polynucleotides include polynucleotides which contain synthetic, non-naturally occurring nucleosides e.g., locked nucleic acids. Modifications to polynucleotides may be utilized to increase or decrease stability of an RNA. An example of a modified polynucleotide is an mRNA containing 1-methyl pseudo-uridine. For examples of modified polynucleotides and their uses, see U.S. Pat. No. 8,278,036. PCT International Publication No. WO/2015/006747, and Weissman and Kariko, 2015, (9):1416-7, hereby incorporated by reference.

In embodiments of the present invention, the guide sequence portion may be 22 nucleotides in length and consists of 22 nucleotides in the sequence of 22 contiguous nucleotides set forth in any one of SEQ ID NOs: 1-20465 of that length. In embodiments of the present invention, the guide sequence portion may be less than 22 nucleotides in length. For example, in embodiments of the present invention the guide sequence portion may be 17, 18, 19, 20, or 21 nucleotides in length. In such embodiments the guide sequence portion may consist of 17, 18, 19, 20, or 21 nucleotides, respectively, in the sequence of 17-22 contiguous nucleotides set forth in any one of SEQ ID NOs: 1-20465. For example, a guide sequence portion having 17 nucleotides in the sequence of 17 contiguous nucleotides set forth in a presently disclosed sequence may consist of any one of the following nucleotide sequences (nucleotides excluded from the contiguous sequence are marked in strike-through):

```
                                (SEQ ID NO: 20466)
     AAACUGACACCUCAGGGACA 17 nucleotide guide sequence 1:
                                (SEQ ID NO: 20467)
     A̶A̶A̶CUGACACCUCAGGGACA 17 nucleotide guide sequence 2:
                                (SEQ ID NO: 20468)
     A̶A̶ACUGACACCUCAGGGACA 17 nucleotide guide sequence 3:
                                (SEQ ID NO: 20469)
     A̶AACUGACACCUCAGGGA C̶A̶

17 nucleotide guide sequence 4:
                                (SEQ ID NO: 20470)
     AAACUGACACCUCAGGG A̶C̶A̶
```

In embodiments of the present invention, the guide sequence portion may be greater than 20 nucleotides in length. For example, in embodiments of the present invention the guide sequence portion may be 21, 22, 23, 24, or 25 nucleotides in length. In such embodiments the guide sequence portion comprises 20, 21 or 22 nucleotides in the sequence of 20, 21, or 22 contiguous nucleotides as set forth in any one of SEQ ID NOs: 1-20465 of that length and additional nucleotides fully complimentary to a nucleotide or sequence of nucleotides adjacent to the 3' end of the target sequence, 5' end of the target sequence, or both.

In embodiments of the present invention, a CRISPR nuclease and an RNA molecule comprising a guide sequence portion form a CRISPR complex that binds to a target DNA sequence to affect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule comprising a guide sequence portion of the present invention, and a tracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek (2012) Science). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base-pairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See U.S. Pat. No. 8,906, 616). In embodiments of the present invention, the RNA molecule may further comprise a portion having a tracr mate sequence.

According to embodiments of the present invention, an RNA molecule may be up to 500, 400, 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

A skilled artisan will appreciate that in each of the embodiments of the present invention, individually, each of the RNA molecules of the present invention are capable of complexing with a nuclease, e.g. a CRISPR nuclease, such as to associate with a target genomic DNA sequence of interest next to a protospacer adjacent motif (PAM). The nuclease then induces cleavage of target DNA to create a double-stranded break within the protospacer. Accordingly, in embodiments of the present invention, the guide sequences and RNA molecules of the present invention may target a location 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from a PAM site.

Therefore, in embodiments of the present invention, the RNA molecules of the present invention in complex with a nuclease, e.g., a CRISPR nuclease, may affect a double strand break in alleles of a gene 1, 2, 3, 4, 5, 6, 7, 8, 9, 10, 11, 12, 13, 14, 15, 16, 17, 18, 19, 20, 21, 22, 23, 24, 25, 26, 27, 28 upstream or downstream from a target site.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

The term "single nucleotide polymorphism (SNP) position", as used herein, refers to a position in which a single nucleotide DNA sequence variation occurs between members of a species, or between paired chromosomes in an individual. In the case that a SNP position exists at paired chromosomes in an individual, a SNP on one of the chromosomes is a "heterozygous SNP." The term SNP position refers to the particular nucleic acid position where a specific variation occurs and encompasses both a sequence including the variation from the most frequently occurring base at the particular nucleic acid position (also referred to as "SNP" or alternative "ALT") and a sequence including the most frequently occurring base at the particular nucleic acid position (also referred to as reference, or "REF"). Accordingly, the sequence of a SNP position may reflect a SNP (i.e. an alternative sequence variant relative to a consensus reference sequence within a population), or the reference sequence itself.

"Eukaryotic" cells include, but are not limited to, fungal cells (such as yeast), plant cells, animal cells, mammalian cells and human cells.

As used herein, the term "HSPC" refers to both hematopoietic stem cells and hematopoietic stem progenitor cells. Non-limiting examples of stem cells include a bone marrow cell, a myeloid progenitor cell, a multipotent progenitor cell, a lineage restricted progenitor cell.

As used herein, "progenitor cell" refers to a lineage cell that is derived from stem cell and retains mitotic capacity and multipotency (e.g., can differentiate or develop into more than one but not all types of mature lineage of cell). As used herein "hematopoiesis" or "haemopoiesis" refers to the formation and development of various types of blood cells (e.g., red blood cells, megakaryocytes, myeloid cells (e.g., monocytes, macrophages and neutrophil), and lymphocytes) and other formed elements in the body (e.g., in the bone marrow).

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

The term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-strand or single strand break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence. DNA repair pathways, including but not limited to HDR, play a role in targeted genome modification, which is a powerful tool that can be used to reverse the effect of pathogenic genetic variations and therefore has the potential to provide new therapies for human genetic diseases. Current genome engineering tools, including engineered zinc finger nucleases (ZFNs), transcription activator-like effector nucleases (TALENs), and most recently, RNA-guided DNA endonucleases such as CRISPR/Cas, produce sequence-specific DNA breaks in a genome. The modification of the genomic sequence occurs at the next step and is the product of the activity cellular DNA repair mechanisms triggered in response to the newly formed DNA break. These mechanisms include, for example: (1) classical non-homologous end-joining (NHEJ) in which the two ends of the break are ligated together in a fast but also inaccurate manner (i.e. frequently resulting in mutation of the DNA at the cleavage site in the form of small insertion or deletions) and (2) homology-directed repair (HDR) in which an intact homologous DNA donor is used to replace the DNA surrounding the cleavage site in an accurate manner. In addition and as discussed above, HDR can also mediate the precise insertion of external or endogenous DNA at the break site.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. A nucleic acid template may be a single stranded nucleic acid, a double stranded nucleic acid. In some embodiment, the nucleic acid template comprises a nucleotide sequence, e.g., of one or more nucleotides, that corresponds to wild type sequence of the target nucleic acid, e.g., of the target position. In some embodiments, the nucleic acid template comprises a ribonucleotide sequence, e.g., of one or more ribonucleotides, that corresponds to wild type sequence of the target nucleic acid, e.g., of the target position. In some embodiment, the nucleic acid template comprises modified ribonucleotides.

Insertion of an exogenous sequence (also called a "donor sequence," donor template" or "donor"), for example, for correction of a mutant gene or for increased expression of a wild-type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620A1. As disclosed in U.S. Publication No. 2019/0330620A1, donor sequence may be encoded on the same molecule as a guide RNA sequence. See Anzolne et al. (2019) Nature 576:149-157. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor may be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 20080159996; 201000218264; 20100291048; 20120017290; 20110265198; 20130137104; 20130122591; 20130177983 and 20130177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual, or a portion thereof, or an alternate version of a gene encoding a protein, or a portion thereof), a regulatory sequence and/or a sequence that encodes a structural nucleic acid such as a microRNA or siRNA.

One aspect of the present disclosure provides a method for utilizing a guide sequence to target a CRISPR nuclease to affect a DSB to modify an allele of a gene bearing a disease associated mutation ('mutant allele'). In some embodiments, at least one naturally occurring nucleotide difference or polymorphism (e.g., single nucleotide polymorphism (SNP)) and/or a disease associated mutation is utilized for targeting one of two alleles of a gene which is an allele bearing a mutation causing a disease phenotype ('mutant allele') rather than a functional/wildtype allele. In some embodiments, a SNP position is utilized for distinguishing/discriminating between two alleles of a gene, an allele bearing a disease associated mutation and a particular sequence (SNP/REF) in the SNP position, and a functional/wild type allele bearing a different sequence in the SNP position. In some embodiments, a disease associated mutation is utilized for distinguishing/discriminating between two alleles of a gene, an allele bearing the disease associated mutation, and a wildtype mutant allele not bearing the same disease associated mutation or bearing a different disease associated mutation. In other embodiments, a non-coding region of the gene common to both the mutant allele and the functional allele is targeted. In some embodiments, the method is for treating, ameliorating, or preventing a dominant haploinsufficiency genetic disorder. In some embodiments, the method further comprises the step of allele cleavage by a CRISPR nuclease. The allele cleavage is selected from the group consisting of: a double strand break (DSB) and a single strand break. In some embodiments, the allele cleavage is a DSB. In some embodiments, the method further comprises the step of correction of the allele such that the corrected allele results in an expression of a functional protein. In some embodiments, the correction is performed by homology directed repair (HDR). In some embodiments, the method further comprises the step of editing/correcting/modifying a sequence of the mutant allele such as to allow expression of a functional protein. In some embodiments, the method further comprises the step of editing/correcting/modifying sequences of the two alleles such as to allow expression of a functional protein.

According to embodiments of the present invention, there is provided a method for modifying in a cell a mutant allele of the Ribosomal Protein S19 (RPS19) having a mutation associated with Diamond Blackfan anemia (DBA), the method comprising introducing to the cell a composition comprising:

a CRISPR nuclease or a sequence encoding the CRISPR nuclease; and a first RNA molecule comprising a guide sequence portion having 17-25 nucleotides or a nucleotide sequence encoding the same, wherein a complex of the CRISPR nuclease and the first RNA molecule affects a double strand break in the mutant allele of the RPS19 gene.

In some embodiments, the first RNA molecule targets the CRISPR nuclease to the mutation associated with DBA.

In some embodiments, the mutation associated with DBA is any one of 19:41859951_T_C; 19:41860011_C_T; 19:41860139_G_T; 19:41860151_C_T; 19:41860216_C_T; 19:41860280_A_G; 19:41860303_C_T; 19:41860766_C_A; 19:41860768_C_T; 19:41860777_G_T; 19:41860817_G_T; 19:41860823_G_C; 19:41860842_A_G; 19:41860853_TG_T; 19:41861111_G_A; 19:41861138_G_A; 19:41861144_A_AT; 19:41861166_CAA_C; 19:41861179_C_T; 19:41861204_C_T; 19:41861217_G_C; 19:41869029_A_G: 19:41869033_TC_CT; 19:41869036_A_C; 19:41869042_C_T; 19:41869043_G_A; 19:41869066_G_A; 19:41869108_A_T; 19:41869138_C_T; 19:41869140_A_AGG: 19:41869151_GTGTG_GTGTGTG: 19:41869152 TTTG; 19:41869162_CG_C; 19:41869166_T_A; 19:41869192_A_ATGG; 19:41869217_A_C: 19:41869708_A_ACT; 19:41869722_G_A: 19:41869724_CAA_C; 19:41869724_C_T; 19:41869748_G_T: 19:41869752_A_G; or 19:41869755_T_C.

In some embodiments, the guide sequence portion of the first RNA molecule comprises a guide sequence of 17-25 contiguous nucleotides containing nucleotides in the sequence set forth in any one of SEQ ID NOs 1-20465 which targets a mutation associated with DBA.

In some embodiments, the first RNA molecule targets the CRISPR nuclease to a SNP position of the mutant allele.

In some embodiments, the SNP position is in anon-coding region of the RPS19 gene at a location that is 250 or fewer nucleotides from the first or the last nucleotide of a coding region of the RPS19 gene containing the mutation associated with DBA.

In some embodiments, the SNP position is located at any one of 19:41860325_C_T; 19:41869228_A_G; 19:41869823_T_C, rs1385169206; rs2075749; rs2075750; or rs2075754.

In some embodiments, the guide sequence portion of the first RNA molecule comprises a guide sequence having 17-25 contiguous nucleotides containing nucleotides in the sequence set forth in any one of SEQ ID NOs 1-20465 which targets a sequence in a SNP position of the mutant allele.

In some embodiments, the SNP position contains a heterozygous SNP.

According to embodiments of the present invention, the RNA molecule targets a particular sequence (SNP/REF) in a SNP position or a disease-causing mutation of a mutant allele.

In some embodiments, the SNP position is in a promoter region, the start codon, an untranslated region (UTR), an intron, an exon, a downstream sequence of a mutant allele. Each possibility represents a separate embodiment. In some embodiments, the SNP position is in a distance of less than 2000 nucleotides, 15000 nucleotides, 1000 nucleotides, 750 nucleotides, 500 nucleotides, 400 nucleotides, 300 nucleotides, 250 nucleotides, 200 nucleotides, 150 nucleotides, or 50 nucleotides from the disease-associated mutation. Each possibility represents a separate embodiment.

In some embodiments, a complex of the CRISPR nuclease and the first RNA molecule affects a double strand break in a non-coding region common to both alleles of the RPS19 gene at a location that is 500, 450, 400, 350, 300, 250 or fewer nucleotides from the first or the last nucleotide of a coding region of the RPS19 gene containing the mutation associated with DBA. Each possibility represents a separate embodiment.

In some embodiments, the non-coding region is upstream of exon 1, upstream of exon 2, upstream of exon 3, upstream of exon 4, upstream of exon 5, upstream of exon 6, downstream of exon 1, downstream of exon 2, downstream of exon 3, downstream of exon 4, downstream of exon 5, or downstream of exon 6.

In some embodiments, the guide sequence portion of the first RNA molecule comprises 17-25 contiguous nucleotides containing nucleotides in the sequence set forth in any one of SEQ ID NOs 1-20465 which targets a non-coding region of the RPS19 gene.

In some embodiments, further comprising introduction of a donor DNA template for homology directed repair (HDR), alteration, or replacement of a desired sequence of the RPS19 allele. Accordingly, this method of modifying a RPS19 pathogenic mutation via HDR corrects the dominant haploinsufficiency disorder that manifests as DBA.

In embodiments of the present invention, the target sequence is in the coding region bearing the mutation associated with DBA or is the entire coding region bearing the mutation associated with DBA.

In embodiments of the present invention, the modifying results in correction of the mutant allele of the RPS19 gene from the mutant phenotype to a non-mutant phenotype.

Embodiments of the present invention further comprise obtaining the cell with an RPS19 gene mutation associated with DBA from a subject with an RPS19 gene mutation related to DBA and/or suffering from DBA.

Embodiments of the present invention further comprise first selecting a subject with an RPS19 gene mutation related to DBA and/or suffering from DBA.

Embodiments of the present invention further comprise obtaining the cell from the subject by mobilization and/or by apheresis.

Embodiments of the present invention further comprise obtaining the cell from the subject by bone marrow aspiration.

In embodiments of the present invention, the cell is prestimulated prior to introducing the composition to the cell.

Embodiments of the present invention further comprise culture expanding the cell to obtain cells.

In embodiments of the present invention, the cells are cultured with one or more of stem cell factor (SCF), IL-3, and GM-CSF.

In embodiments of the present invention, the cells are cultured with at least one cytokine.

In embodiments of the present invention, the at least one cytokine is a recombinant human cytokine.

In embodiments of the present invention, the cell is among a plurality of cells, wherein the composition comprising the first RNA molecule and/or donor DNA template is introduced into at least the cell as well as other cells among the plurality of cells, and the mutant allele of the RPS19 gene is modified in at least the cell as well as in the other cells among the plurality of cells, thereby obtaining multiple modified cells.

In embodiments of the present invention, introducing the composition comprising the first RNA molecule and/or introduction of the donor DNA template comprises electroporation of the cell or cells.

The present invention provides for a modified cell obtained by the methods of the present invention.

The present invention provides for modified cells obtained from culture expanding the modified cell obtained by the methods of the present invention.

In embodiments of the present invention, the modified cell or cells are capable of engraftment.

In embodiments of the present invention, the modified cell or cells are capable of giving rise to progeny cells.

In embodiments of the present invention, the modified cell or cells are capable of giving rise to progeny cells after engraftment.

In embodiments of the present invention, the modified cell or cells are capable of giving rise to progeny cells after an autologous engraftment.

In embodiments of the present invention, the modified cell or cells are capable of giving rise to progeny cells for at least 12 months or at least 24 months after engraftment.

In embodiments of the present invention, the modified cell or cells are hematopoietic stem cells and/or progenitor cells (HSPCs).

In embodiments of the present invention, the modified cell or cells are CD34+ hematopoietic stem cells.

In embodiments of the present invention, the modified cell or cells are bone marrow cells or peripheral mononucleated cells (PMCs).

The present invention provides for a composition comprising the modified cells of the present invention and a pharmaceutically acceptable carrier.

In embodiments of the present invention, an in vitro or ex vivo method of preparing the compositions of the present invention, comprising mixing the cells with the pharmaceutically acceptable carrier.

The present invention provides for a method of preparing in vitro or ex vivo a composition comprising modified cells, the method comprising:
a) isolating HSPCs from cells obtained from a subject with an RPS19 gene mutation related to DBA and/or suffering from DBA, and obtaining the cell from the subject;
b) introducing to the cells of step (a) a composition comprising:
a CRISPR nuclease or a sequence encoding the CRISPR nuclease; and
a first RNA molecule comprising a guide sequence portion having 17-25 nucleotides,
wherein a complex of the CRISPR nuclease and the first RNA molecule affects a double strand break in the mutant allele of the RPS19 gene according to any one of the methods of the invention,
optionally, introducing to the cells a donor DNA template for homology directed repair (HDR), alteration, or replacement of a target sequence of the RPS19 allele
so as to modify the mutant allele of the RPS19 gene in one or more cells thereby obtaining modified cells; optionally
c) culture expanding the modified cells of step (b), wherein the modified cells are capable of engraftment and giving rise to progeny cells after engraftment.

The present invention provides for use of a composition prepared in vitro by a method comprising:
a) isolating HSPCs from cells obtained from a subject with an RPS19 gene mutation related to DBA and/or suffering from DBA, and obtaining the cell from the subject;
b) introducing to the cells of step (a) a composition comprising:
a CRISPR nuclease or a sequence encoding the CRISPR nuclease; and
a first RNA molecule comprising a guide sequence portion having 17-25 nucleotides,
wherein a complex of the CRISPR nuclease and the first RNA molecule affects a double strand break in the mutant allele of the RPS19 gene according to any one of the methods of the invention,
optionally, introducing to the cells a donor DNA template for homology directed repair (HDR), alteration, or replacement of a target sequence of the RPS19 allele
so as to modify the mutant allele of the RPS19 gene in one or more cells thereby obtaining modified cells; optionally;
c) culture expanding the cells of step (b) wherein the modified cells are capable of engraftment and giving rise to progeny cells after engraftment; and
d) administering to the subject the cells of step (b) or step (c)
for treating the DBA in the subject.

The present invention provides for a method of treating a subject afflicted with DBA, comprising administration of a therapeutically effective amount of the modified cells of the present invention, the compositions of the present invention, or the composition prepared by the methods of the present invention.

The present invention provides for a method for treating DBA in a subject with an RPS19 gene mutation relating to DBA in need thereof, the method comprising:
a) isolating HSPCs from cells obtained from the subject;
b) introducing to the cells of step (a) a composition comprising:
a CRISPR nuclease or a sequence encoding the CRISPR nuclease; and
a first RNA molecule comprising a guide sequence portion having 17-25 nucleotides,
wherein a complex of the CRISPR nuclease and the first RNA molecule affects a double strand break in the mutant allele of the RPS19 gene according to any one of the methods of the invention,
optionally, introducing to the cells a donor DNA template for homology directed repair (HDR), alteration, or replacement of a target sequence of the RPS19 allele
so as to modify the mutant allele of the RPS19 gene in one or more cells thereby obtaining modified cells; optionally;
c) culture expanding the cells of step (b) wherein the modified cells are capable of engraftment and giving rise to progeny cells after engraftment; and
d) administering to the subject the cells of step (b) or step (c)
thereby treating the DBA in the subject.

The present invention provides for a method for treating DBA in a subject with an RPS19 gene mutation relating to DBA in need thereof, the method comprising
administering to the subject autologous modified cells or progeny of autologous modified cells, wherein the autologous modified cells are modified so as to have a correction of the mutant allele of the RPS19 gene from the mutant phenotype to a non-mutant phenotype, wherein said double strand break results from introduction to the cells of a composition comprising a CRISPR nuclease or sequence encoding the CRISPR nuclease and a first RNA molecule wherein a complex of the CRISPR nuclease and the first RNA molecule affects a double strand break in the mutant allele of the RPS19 gene according to any one of the methods of the invention, thereby treating the DBA in the subject.

The present invention provides for an RNA molecule comprising a guide sequence portion having 17-25 contiguous nucleotides containing nucleotides in the sequence set forth in any one of SEQ ID NOs 1-20465.

In embodiments of the present invention, the RNA molecule further comprises a portion having a sequence which binds to a CRISPR nuclease.

In embodiments of the present invention, the sequence which binds to a CRISPR nuclease is a tracrRNA sequence.

In embodiments of the present invention, the RNA molecule further comprises one or more linker portions.

In embodiments of the present invention, the RNA molecule further comprises a portion having a tracr mate sequence.

In embodiments of the present invention, the RNA molecule is up to 300 nucleotides in length.

According to embodiments of the present invention, the RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 30 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

The present invention provides for a composition comprising the RNA molecules of the present invention and a donor DNA template for homology directed repair (HDR), alteration, or replacement of a target sequence of the RPS19 allele.

In embodiments of the present invention, the composition further comprises one or more CRISPR nucleases or sequences encoding the one or more CRISPR nucleases, and/or one or more tracrRNA molecules or sequences encoding the one or more tracrRNA molecules.

The present invention provides for a method for modifying in a cell a mutant allele of the RPS19 gene, the method comprising delivering to the cell the RNA molecules of the present invention or the compositions of the present invention.

The present invention provides for a method for treating DBA, the method comprising delivering to a subject having DBA the RNA molecules of the present invention or the compositions of the present invention, or cells modified by the RNA molecules of the present invention or the compositions of the present invention.

In embodiments of the present invention, the one or more CRISPR nucleases and/or the tracrRNA and the RNA molecule are delivered to the subject and/or cells substantially at the same time or at different times.

In embodiments of the present invention, the modifying or treating results in a functional protein encoded by both alleles of the RPS19 gene.

The present invention provides for use of the RNA molecules of the present invention, the compositions of the present invention, or the composition prepared by the methods of the present invention, for modifying in a cell a mutant RPS19 allele.

The present invention provides for a medicament comprising the RNA molecules of the present invention, the compositions of the present invention, or the composition prepared by the methods of the present invention for use in inactivating in a cell a mutant RPS19 allele, wherein the medicament is administered by delivering to the cell the RNA molecules of the present invention, the compositions of the present invention, or the composition prepared by the methods of the present invention.

The present invention provides for use of the methods of the present invention, the modified cells of the present invention, the compositions of the present invention, or the compositions prepared by the methods of the present invention, or the RNA molecules of the present invention for treating ameliorating or preventing DBA in to a subject having or at risk of having DBA.

The present invention provides for a medicament comprising the RNA molecules of the present invention, the compositions of the present invention, the compositions prepared by the methods of the present invention, or the modified cells of the present invention, for use in treating ameliorating or preventing DBA, wherein the medicament is administered by delivering to a subject having or at risk of having DBA the RNA molecules of the present invention, the compositions of the present invention, the compositions prepared by the methods of the present invention, or the modified cells of the present invention.

The present invention provides for a kit for inactivating a mutant RPS19 allele in a cell, comprising an RNA molecule of the present invention, a CRISPR nuclease or a sequence encoding the CRISPR nuclease, and/or a tracrRNA molecule or a sequence encoding the tracrRNA; and instructions for delivering the RNA molecule; CRISPR nuclease or a sequence encoding the CRISPR nuclease, and/or the tracrRNA molecule or a sequence encoding the tracrRNA to the cell to modify the mutant RPS19 allele in the cell.

The present invention provides for a kit for treating DBA in a subject, comprising an RNA molecule of the present invention, a CRISPR nuclease or a sequence encoding the CRISPR nuclease, and/or a tracrRNA molecule or a sequence encoding the tracrRNA; and instructions for delivering the RNA molecule; CRISPR nuclease or sequence encoding the CRISPR nuclease, and/or tracrRNA molecule or sequence encoding the tracrRNA to a subject having or at risk of having DBA so as to treat the DBA.

The present invention provides for a kit for inactivating a mutant RPS19 allele in a cell, comprising the compositions of the present invention, the compositions prepared by the methods of the present invention, or the modified cells of the present invention, and instructions for delivering the composition to the cell so as to modify the RPS19 gene in the cell.

The present invention provides for a kit for treating DBA in a subject, comprising the compositions of the present invention, the compositions prepared by the methods of the present invention, or the modified cells of the present invention, and instructions for delivering the compositions of the present inventions, the compositions prepared by the methods of the present invention, or the modified cells of the present invention, to a subject having or at risk of having DBA so as to treat DBA.

According to some embodiments of the present invention, there is provided a kit for repairing/correcting/modifying a mutant DBA allele in a cell(s), comprising an RNA molecule comprising a guide sequence portion having 17-25 contiguous nucleotides containing nucleotides in the sequence set forth in any one of SEQ ID NOs 1-20465, a CRISPR nuclease, and/or a tracrRNA molecule; and instructions for delivering the RNA molecule; CRISPR nuclease, and/or the tracrRNA to the cell. In some embodiments, the kit further comprises, a nucleic acid template for homology-directed repair, alteration, or replacement of at least a portion of a target gene.

According to some embodiments of the present invention, there is provided a kit for treating DBA in a subject, comprising an RNA molecule comprising a guide sequence portion having 17-25 contiguous nucleotides containing nucleotides in the sequence set forth in any one of SEQ ID NOs 1-20465, a CRISPR nuclease, and/or a tracrRNA molecule; and instructions for delivering the RNA molecule; CRISPR nuclease, and/or the tracrRNA to a subject having or at risk of having DBA. In some embodiments, the kit further comprises, a nucleic acid template for homology-directed repair, alteration, or replacement of at least a portion of a target gene.

The present invention provides for a method for selecting a subject for treatment of DBA from a pool of subjects diagnosed with DBA, comprising the steps of:
  a) obtaining cells from each subject in the pool of subjects;
  b) screening each subjects cells for an RPS19 gene mutation related to DBA and selecting only subjects with an RPS19 gene mutation related to DBA;
  c) screening by sequencing the cells of subjects selected in step (b) for heterozygosity at one or more polymorphic sites selected from the group consisting of 19:41860325_C_T; 19:41869228_A_G; 19:41869823_T_C, rs1385169206; rs2075749; rs2075750; and rs2075754; and
  d) selecting for treatment only subjects with cells that are heterozygous at the one or of the more polymorphic sites.

The present invention provides for a method for selecting a subject for treatment of DBA from a pool of subjects diagnosed with DBA, comprising the steps of:
  a) obtaining cells from each subject in the pool of subjects; and
  b) screening each subject's cells for an RPS19 gene mutation related to DBA and selecting only subjects with an RPS19 gene mutation related to DBA.
  c) According to some embodiments of the present invention, there is provided a method for treating DBA, the method comprising delivering to a subject or cell(s) obtained from a subject having DBA or at risk of DBA a composition comprising an RNA molecule comprising a guide sequence portion having 17-25 contiguous nucleotides containing nucleotides in the sequence set forth in any one of SEQ ID NOs 1-20465 and a CRISPR nuclease.

According to embodiments of the present invention, there is provided a medicament comprising an RNA molecule comprising a guide sequence portion having 17-25 contiguous nucleotides containing nucleotides in the sequence set forth in any one of SEQ ID NOs 1-20465 and a CRISPR nuclease for use in repairing/correcting/modifying a mutant RPS19 allele in a cell, wherein the medicament is administered by delivering to the cell the composition comprising an RNA molecule comprising a guide sequence portion having 17-25 contiguous nucleotides containing nucleotides in the sequence set forth in any one of SEQ ID NOs 1-20465 and a CRISPR nuclease.

According to some embodiments of the present invention, there is provided use of a composition comprising an RNA molecule comprising a guide sequence portion having 17-25 contiguous nucleotides containing nucleotides in the sequence set forth in any one of SEQ ID NOs 1-20465 and a CRISPR nuclease for treating ameliorating or preventing DBA, comprising delivering to a subject having or at risk of having DBA the composition of comprising an RNA molecule comprising a guide sequence portion having 17-25 contiguous nucleotides containing nucleotides in the sequence set forth in any one of SEQ ID NOs 1-20465 and a CRISPR nuclease.

According to some embodiments of the present invention, there is provided a medicament comprising the composition comprising an RNA molecule comprising a guide sequence portion having 17-25 contiguous nucleotides containing nucleotides in the sequence set forth in any one of SEQ ID NOs 1-20465 and a CRISPR nuclease for use in treating ameliorating or preventing DBA, wherein the medicament is administered by delivering to a subject having or at risk of having DBA: the composition comprising an RNA molecule comprising a guide sequence portion having 17-25 contiguous nucleotides containing nucleotides in the sequence set forth in any one of SEQ ID NOs 1-20465 and a CRISPR nuclease. In some embodiments, the medicament further comprises, a nucleic acid template for homology-directed repair, alteration, or replacement of at least a portion of a target gene.

The compositions and methods of the present disclosure may be utilized for treating, preventing, ameliorating, or slowing progression of DBA.

In some embodiments, the method of repairing/correcting a mutant allele further comprises enhancing activity of the functional protein such as by providing a protein/peptide, a nucleic acid encoding a protein/peptide, or a small molecule such as a chemical compound, capable of activating/enhancing activity of the functional protein.

In embodiments of the present invention, the guide sequence portion of the first RNA molecule comprises 17-25 contiguous nucleotides containing nucleotides in the sequence set forth in any one of SEQ ID NOs 1-20465.

According to some embodiments of the present invention, there is provided a composition comprising an RNA molecule comprising a guide sequence portion having 17-25 contiguous nucleotides containing nucleotides in the sequence set forth in any one of SEQ ID NOs 1-20465 and a CRISPR nuclease.

According to embodiments of the present invention, the composition may comprise a nucleic acid template for homology-directed repair, alteration, or replacement of a target DNA sequence comprising the pathogenic mutation (e.g., an allele bearing a disease-associated mutation, or an allele bearing a disease-associated mutation and a particular sequence SNP/REF in the SNP position).

According to some embodiments of the present invention, there is provided a method for repairing/correcting a mutant RPS19 allele in a cell, the method comprising delivering to the cell a composition comprising an RNA molecule comprising a guide sequence portion having 17-25 contiguous nucleotides containing nucleotides in the sequence set forth in any one of SEQ ID NOs 1-20465 and a CRISPR nuclease.

In anon-limiting example, an RNA molecule comprising a guide sequence is utilized to direct a CRISPR nuclease to a mutant allele and create a double-strand break (DSB) and correction/repair of the mutant allele is further performed, such as by utilizing homology directed repair (HDR), which incorporates a homologous strand as a repair template.

According to embodiments of the present invention, the CRISPR nuclease and the RNA molecule or RNA molecules are delivered to the subject and/or cells obtained from the subject substantially at the same time or at different times.

According to embodiments of the present invention, the tracrRNA is delivered to the subject and/or cells obtained from the subject substantially at the same time or at different times as the CRISPR nuclease and RNA molecule or RNA molecules.

According to embodiments of the present invention, the nucleic acid template is delivered to the subject and/or cells obtained from the subject substantially at the same time or at different times as the CRISPR nuclease and RNA molecule or RNA molecules.

In some embodiments, there is provided a method comprising removing an exon containing a disease-causing mutation from a mutant allele, wherein the RNA molecule or a first and a second RNA molecules target regions flanking an entire exon or a portion of the exon or multiple exons or the entire open reading frame of a gene, or the entire gene. In some embodiments, the method includes exon skipping. In some embodiments, the method further comprises, utilizing a nucleic acid template for homology-directed repair, alteration, or replacement of the entire exon or a portion of the exon or multiple exons or the entire open reading frame of a gene, or the entire gene. Alternatively, repair of the mutant allele sequence is template free.

According to embodiments of the present invention, the method comprises subjecting the mutant allele to error prone non-homologous end joining (NHEJ) mechanism. According to preferred embodiments of the present invention, the method comprises correction or repair of a mutant allele with a template via a homology-directed repair mechanism after a targeted double-strand break in order to remove the haploinsufficiency manifestations of the mutant allele.

According to some embodiments of the present invention, there is provided use of a composition comprising an RNA molecule comprising a guide sequence portion having 17-25 contiguous nucleotides containing nucleotides in the sequence set forth in any one of SEQ ID NOs 1-20465 and a CRISPR nuclease repairing/correcting/modifying a mutant RPS19 allele in a cell, comprising delivering to the cell the RNA molecule comprising a guide sequence portion having 17-25 contiguous nucleotides containing nucleotides in the sequence set forth in any one of SEQ ID NOs 1-20465 and the CRISPR nuclease.

In embodiments of the present invention, the RNA molecule comprises a guide sequence portion having 17-25 contiguous nucleotides containing nucleotides in the sequence set forth in any one of SEQ ID NOs 1-20465.

One aspect of the present invention also provides for a method for modifying in a cell a mutant allele of the Ribosomal Protein S19 gene (RPS19 gene) having a mutation associated with Diamond Blackfan anemia (DBA), the method comprising
   introducing to the cell a composition comprising:
      a CRISPR nuclease or a sequence encoding the CRISPR nuclease; and
      a first RNA molecule comprising a guide sequence portion having 17-25 nucleotides or a nucleotide sequence encoding the same,
   wherein a complex of the CRISPR nuclease and the first RNA molecule affects a double strand break in a non-coding region of the RPS19 gene at a location that is 250 or fewer nucleotides from the first or the last nucleotide of a coding region of the RPS19 gene containing the mutation associated with DBA.

One aspect of the present invention also provides for a method for modifying in a cell a mutant allele of the Ribosomal Protein S19 gene (RPS19 gene) having a mutation associated with Diamond Blackfan anemia (DBA), the method comprising
   introducing to the cell a composition comprising:
      a CRISPR nuclease or a sequence encoding the CRISPR nuclease; and
      a first RNA molecule comprising a guide sequence portion having 17-25 nucleotides or a nucleotide sequence encoding the same,
   wherein a complex of the CRISPR nuclease and the first RNA molecule targets the CRISPR nuclease to the mutation associated with DBA.

One aspect of the present invention also provides for a method for modifying in a cell a mutant allele of the Ribosomal Protein S19 gene (RPS19 gene) having a mutation associated with Diamond Blackfan anemia (DBA), the method comprising
   introducing to the cell a composition comprising:
      a CRISPR nuclease or a sequence encoding the CRISPR nuclease; and
      a first RNA molecule comprising a guide sequence portion having 17-25 nucleotides or a nucleotide sequence encoding the same,
   wherein a complex of the CRISPR nuclease and the first RNA molecule targets the CRISPR nuclease to a SNP position of the mutant allele.

Embodiments of the present invention further comprise introduction of a donor DNA template for homology directed repair (HDR), alteration, or replacement of a target sequence of the RPS19 allele. In some embodiments, the donor DNA template for HDR (e.g., dsDNA or ssODN) is at least 10, 20, 30, 40, 50, 100, 200, 300, 400, 500, 600, 700, 800, 1,000, 1,250, 1,500, 2,000, 3,000, or 5,000 base pairs in length, at most 20, 30, 40, 50, 100, 200, 300, 400, 500, 600, 700, 800, 1,000, 1,250, 1,500, 2,000, 3,000, or 5,000 base pairs in length, or between 10 and 5000, 10 and 3000, 10 and 2000, 10 and 1000, 10 and 500, 10 and 400, 10 and 300, 10 and 200, 10 and 100, 10 and 60, 10 and 50, 20 and 5000, 20 and 3000, 20 and 2000, 20 and 1000, 20 and 500, 20 and 400, 20 and 300, 20 and 200, 20 and 100, 20 and 60, 20 and 50, 30 and 5000, 30 and 3000, 30 and 2000, 30 and 1000, 30 and 500, 30 and 400, 30 and 300, 30 and 200, 30 and 100, 30 and 60, or 30 and 50 base pairs in length. Each possibility represents a separate embodiment. In some embodiments, the donor DNA template for HDR overlaps in sequence complementarity with regions upstream and downstream double-strand break site induced by a nuclease programmed by any one of the guides described herein. In some embodiments, the donor DNA template for HDR comprises a sequence that overlaps in sequence complementarity with an entire exon or more.

According to some embodiments, the present disclosure provides an RNA sequence ('RNA molecule') which binds to/associates with and/or directs the RNA guided DNA nuclease e.g., CRISPR nuclease to a sequence comprising at least one nucleotide which differs between a mutant allele and a second allele (e.g., functional/wild type allele) of a gene of interest (i.e., a sequence of the mutant allele which is not present in the second allele).

In some embodiments, the method comprises the steps of: contacting a mutant allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutant allele of the gene of interest which differs by at least one nucleotide from a nucleotide sequence of a second allele of the gene of interest (i.e., a functional/wild type allele), thereby modifying the mutant allele.

Treatment of DBA

In embodiments of the present invention, the RNA molecules, compositions, methods, cells, kits, or medicaments are utilized for treating a subject having a disease phenotype resulting from the heterozygote RPS19 gene. In embodiments of the present invention, the disease is DBA. In such embodiments, the method results in improvement, amelioration or prevention of the disease phenotype. Any one of, or combination of, the above-mentioned strategies for bi-allelic cut and correction, or allele-specific targeting based on a heterozygous SNP or mutation sequence, may be used in the context of the invention.

In embodiments of the present invention, the RNA molecules, compositions, methods, cells, kits, or medicaments are utilized for treating a subject having a disease phenotype resulting from the RPS19 gene. In embodiments of the present invention, the disease is Diamond Blackan anemia (DBA). In such embodiments, the method results in improvement, amelioration or prevention of the disease phenotype.

In embodiments of the present invention, the RNA molecules, compositions, methods, cells, kits, or medicaments of the present invention are utilized in combination with a second therapy for DBA to treat the subject. In embodiments of the present invention, the RNA molecules, compositions, methods, kits, or medicaments of the present invention are administered prior to administration of the second therapy, during administration of the second therapy, and/or after administration of the second therapy.

In embodiments of the present invention, a cell with an RPS19 gene mutation associated with DBA may be from a subject with the RPS19 gene mutation and/or afflicted with DBA. Accordingly, selecting a cell with an RPS19 gene mutation may comprise selecting a subject with the RPS19 gene mutation. In further embodiments of the present invention, selecting a cell may comprise selecting a cell from a subject with the RPS19 gene mutation. In embodiments of the present invention, introducing the compositions of the subject invention to the cell may comprise introducing the compositions of the invention to the cell of a subject afflicted with the RPS19 gene mutation.

Accordingly, embodiments of the present invention encompass the screening of subjects or cells for the RPS19 gene. A person having ordinary skill in the art would readily understand methods of screening for mutations within the RPS19 gene in the art, by way of non-limiting examples, e.g., sequencing-by-synthesis, Sanger sequencing, karyotyping, Fluorescence In situ Hybridization, and/or microarray testing. In embodiments of the present invention, mutations within the RPS19 gene are screened by exon sequencing. In one embodiment of the invention, a subject is screened for heterozygous DBA mutation or SNPs prior to treatment with a composition that includes guide sequences of the present invention.

In embodiments of the present invention, a subject diagnosed with DBA is screened by Exon sequencing to identify an RPS19 pathogenic mutation in the RPS19 gene.

It is understood that the CRISPR/Cas9 gene editing system enables targeting the nuclease to a target site in a sequence specific manner to address disease-causing mutations. Hematopoietic stem and progenitor cells (HSPCs) have therapeutic potential because of their ability to both self-renew and differentiate (Yu, Natanson, and Dunbar 2016). Accordingly, embodiments of the present invention apply genome editing to HSPCs.

In embodiments of the present invention, an autologous therapy and utilizes autologous CD34+ hematopoietic stem cells from patients diagnosed with DBA which are edited with CRISPR/Cas9. In embodiments of the present invention, CD34+ cells are isolated from bone marrow or peripheral blood mononucleated cells (PBMCs) following patient apheresis.

In some embodiments, an allele-specific or bi-allelic targeting RNA molecule and a CRISPR nuclease are introduced to a cell encoding the gene of interest. In some embodiments, the cell encoding the gene of interest is in a mammalian subject. In some embodiments, the cell encoding the gene of interest is a eukaryotic cell. In some embodiments, the cell encoding the gene of interest is a mammalian cell.

In some embodiments, a nucleic acid template is further introduced to the cell encoding the gene of interest for homology-directed repair, alteration, or replacement of a target sequence of the gene of interest to correct/repair the gene of interest such as to express a functional protein.

In some embodiments, the mutant allele desired to be targeted for correction or modification is an allele of the RPS19 gene. In some embodiments, the RNA molecule targets a SNP which co-exists with or is genetically linked to the disease-causing mutation associated with DBA genetic disorder. In some embodiments, the RNA molecule targets a SNP which is highly prevalent in the population and exists in a mutant allele having the mutated sequence associated with DBA genetic disorder and not in a second allele (e.g., functional allele) of an individual subject to be treated. In some embodiments, a disease-causing mutation within a mutated RPS19 allele is targeted. In some embodiments, a non-discriminatory guide sequence targets a noncoding region common to both RPS19 alleles up to 250 base pairs from an exon bearing a pathogenic mutation of interest.

In some embodiments, the method is utilized for treating a subject having a disease phenotype resulting from a mutation in the RPS19 gene. In such embodiments, the method results in improvement, amelioration or prevention of the disease phenotype.

Embodiments referred to above refer to a CRISPR nuclease, RNA molecule(s), and optionally tracrRNA being effective in a subject or cells at the same time. The CRISPR, RNA molecule(s), and optionally tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

In one embodiment, the cell is a stem cell. In one embodiment, the cell is an embryonic stem cell. In some embodiment, the stem cell is a hematopoietic stem/progenitor cell (HSC). As used herein, the term HSC refers to both hematopoietic stem cells and hematopoietic stem progenitor cells. Non-limiting examples of stem cells include bone marrow cells, myeloid progenitor cells, a multipotent progenitor cells, a lineage restricted progenitor cells.

Dominant Genetic Disorders

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of a dominant genetic disorders such as Diamond-Blackfan anemia (DBA). In some embodiments, the genetic disorder is DBA. In some embodiments, the target gene is the RPS19 gene (Entrez Gene, gene ID No: 6223) which is located in chromosome 19 and encodes a ribosomal protein that is a component of the 40S subunit. The protein belongs to the S19E family of ribosomal proteins. Mutations in this gene may cause Diamond-Blackfan anemia (DBA), a constitutional erythroblastopenia characterized by absent or decreased erythroid precursors, in a subset of patients.

Table 1 hereinbelow discloses a non-limiting list of exemplary mutations in the RPS19 gene.

Any of the RPS19 mutations listed in Table 1 may be corrected or modified by one of the following strategies: (1) Utilizing a guide sequence targeting the pathogenic mutation itself to induce a DSB in proximity to the mutation in the mutant allele, and then using HDR for correction; (2) Utilizing a guide sequence targeting a SNP upstream or downstream of the pathogenic mutation listed in Table 1, or upstream or downstream of an exon bearing the pathogenic mutation, and then using HDR for correction; or (3) Utilizing a non-discriminatory guide sequence that targets a non-coding region common to both alleles of the gene and is up to 250 base pairs from an exon bearing a pathogenic mutation listed in Table 1 to induce a DSB in the non-coding region of both alleles, and then using HDR for correction of the mutation and/or correction or replacement of the exon bearing the pathogenic mutation.

Table 1: A non-limiting list of exemplary mutations in the RPS19 gene. The transcript for each of the mutations disclosed is the NM_001022.3 transcript. Mutations positions are indicated based on gnomAD v3 database and UCSC Genome Browser assembly ID: hg38, sequencing/assembly provider ID: Genome reference consortium Human GRCh38.p12 (GCA_00001405.27) Assembly date December 2013 initial release December 2017 patch release 12).

| Mutation position | Transcript Consequence (NM_001022) | NM_001022.4 (RPS19) |
|---|---|---|
| 19:41859951_T/C | c.-339T > C | Exon1 |
| 19:41860011_C/T | c.-279C > G | Exon1 |
| 19:41860139_G/T | c.-151G > T | Exon1 |
| 19:41860151_C/T | c.-139C > T | Exon1 |
| 19:41860216_C/T | c.-74C > T | Exon1 |
| 19:41860280_A/G | c.-10A > G | Exon1 |
| 19:41860303_C/T | c.-1 + 14C > T | Intron1 |
| 19:41860766_C/A | c.1-9C > A | Intron1 |
| 19:41860768_C/T | c.1-7C > T | Intron1 |
| 19:41860773_A/T | c.1-2A > T | Intron1 |
| 19:41860774_G/A | c.1-1G > A | Intron1 |
| 19:41860774_G/C | c.1-1G > C | Intron1 |
| 19:41860774_G/T | c.1-1G > T | Intron1 |
| 19:41860775_A/G | c.1A > G | Exon2 |
| 19:41860776_T/A | c.2T > A | Exon2 |
| 19:41860777_G/A | c.3G > A | Exon2 |
| 19:41860777_G/C | c.3G > C | Exon2 |
| 19:41860777_G/T | c.3G > T | Exon2 |
| 19:41860782_AGATT/A | c.10_13delGTTA | Exon2 |
| 19:41860786_T/TA | c.13_14insA | Exon2 |
| 19:41860787_AC/A | c.14delC | Exon2 |
| 19:41860792_AAAAGACGTGAACC/A | c.20_32del | Exon2 |
| 19:41860797_ACGTGAACCAGCAGGAGTT/A | c.25_42del | Exon2 |
| 19:41860802_T/TT | c.28_29insT | Exon2 |
| 19:41860804_CCAGCAGGAGTTCGT/C | c.34_47del | Exon2 |
| 19:41860805_C/T | c.31C > T | Exon2 |
| 19:41860808_C/T | c.34C > T | Exon2 |

| Mutation position | Transcript Consequence (NM_001022) | NM_001022.4 (RPS19) |
|---|---|---|
| 19:41860808_C/CAG | c.36_37insAG | Exon2 |
| 19:41860817_G/T | c.43G > T | Exon2 |
| 19:41860823_G/C | c.49G > C | Exon2 |
| 19:41860827_T/TAGA | c.53_54insAGA | Exon2 |
| 19:41860827_T/C | c.53T > C | Exon2 |
| 19:41860827_T/G | c.53T > G | Exon2 |
| 19:41860831_AG/A | c.58delG | Exon2 |
| 19:41860832_G/C | c.58G > C | Exon2 |
| 19:41860836_T/C | c.62T > C | Exon2 |
| 19:41860842_A/G | c.68A > G | Exon2 |
| 19:41860844_AAGTG/A | c.71 + 3_71 + 6delGAGT | Intron2 |
| 19:41860846_G/A | c.71 + 1G > A | Intron2 |
| 19:41860846_G/C | c.71 + 1G > C | Intron2 |
| 19:41860853_TG/T | c.71 + 12del | Intron2 |
| 19:41861110_A/C | c.72-2A > C | Intron2 |
| 19:41861111_G/A | c.72-1G > A | Intron2 |
| 19:41861123_T/G | c.83T > G | Exon3 |
| 19:41861127_AG/A | c.88delG | Exon3 |
| 19:41861129_TC/T | c.93delC | Exon3 |
| 19:41861138_G/A | c.98G > A | Exon3 |
| 19:41861141_T/TG | c.103dupG | Exon3 |
| 19:41861143_G/GA | c.104_105insA | Exon3 |
| 19:41861144_A/AT | c.105dup | Exon3 |
| 19:41861145_T/TA | c.106_107insA | Exon3 |
| 19:41861152_A/T | c.112A > T | Exon3 |
| 19:41861166_CAA/C | c.128_129del | Exon3 |
| 19:41861174_TT/AA | c.134_135delinsAA | Exon3 |
| 19:41861176_G/GCT | c.139_140insTC | Exon3 |
| 19:41861179_C/T | c.139C > T | Exon3 |
| 19:41861180_C/T | c.140C > T | Exon3 |
| 19:41861184_C/A | c.144C > A | Exon3 |
| 19:41861194_T/C | c.154T > C | Exon3 |
| 19:41861195_G/A | c.155G > A | Exon3 |
| 19:41861196_G/A | c.156G > A | Exon3 |
| 19:41861196_G/C | c.156G > C | Exon3 |
| 19:41861204_C/T | c.164C > T | Exon3 |
| 19:41861206_C/T | c.166C > T | Exon3 |
| 19:41861207_G/A | c.167G > A | Exon3 |

-continued

| Mutation position | Transcript Consequence (NM_001022) | NM_001022.4 (RPS19) |
|---|---|---|
| 19:41861209_G/C | c.169G > C | Exon3 |
| 19:41861212_G/C | c.172G > C | Exon3 |
| 19:41861213_G/C | c.172 + 1G > C | Intron3 |
| 19:41861213_G/T | c.172 + 1G > T | Intron3 |
| 19:41861217_G/C | c.172 + 5G > C | Intron3 |
| 19:41869023_ACCCCCAGCT/A | c.173-7_174del | Intron3 |
| 19:41869029_AG/A | c.173-1delG | Intron3 |
| 19:41869029_A/G | c.173-2A > G | Intron3 |
| 19:41869029_A/T | c.173-2A > T | Intron3 |
| 19:41869030_G/A | c.173-1G > A | Intron3 |
| 19:41869033_TC/CT | c.175_176delinsCT | Exon4 |
| 19:41869034_C/T | c.176C > T | Exon4 |
| 19:41869036_A/C | c.178A > C | Exon4 |
| 19:41869040_C/A | c.182C > A | Exon4 |
| 19:41869042_C/T | c.184C > T | Exon4 |
| 19:41869043_G/A | c.185G > A | Exon4 |
| 19:41869044_G/GCCA | c.187_188insCAC | Exon4 |
| 19:41869049_T/C | c.191T > C | Exon4 |
| 19:41869053_C/G | c.195C > G | Exon4 |
| 19:41869053_CCTCCGGGGTGG/C | c.197_207del | Exon4 |
| 19:41869058_C/CG | c.203_204insG | Exon4 |
| 19:41869066_G/A | c.208G > A | Exon4 |
| 19:41869070_G/A | c.212G > A | Exon4 |
| 19:41869078_TC/T | c.222delC | Exon4 |
| 19:41869084_A/C | c.226A > C | Exon4 |
| 19:41869087_AAGATCTATGGGGGACGTC/A | c.233_250del | Exon4 |
| 19:41869095_T/TG | c.242_243insG | Exon4 |
| 19:41869105_CAG/C | c.250_251delAG | Exon4 |
| 19:41869107_G/GA | c.250_251insA | Exon4 |
| 19:41869108_A/T | c.250A > T | Exon4 |
| 19:41869131_ACTTCAGCCGAGGCTCCAAGAGTGTGGCCCGC/A | c.274_304del | Exon4 |
| 19:41869138_C/T | c.280C > T | Exon4 |
| 19:41869139_G/T | c.281G > T | Exon4 |
| 19:41869140_A/AGG | c.283_284dupGG | Exon4 |
| 19:41869140_AG/A | c.284delG | Exon4 |
| 19:41869147_A/AAGGC | c.289_290insAGGC | Exon4 |
| 19:41869150_AGT/A | c.295_296delGT | Exon4 |
| 19:41869151_GTGTG/GTGTGTG | c.294_295TG[3] | Exon4 |

-continued

| Mutation position | Transcript Consequence (NM_001022) | NM_001022.4 (RPS19) |
|---|---|---|
| 19:41869152_T/TTG | c.294_295insTG | Exon4 |
| 19:41869159_C/T | c.301C > T | Exon4 |
| 19:41869160_G/A | c.302G > A | Exon4 |
| 19:41869162_CG/C | c.307delG | Exon4 |
| 19:41869163_G/C | c.305G > C | Exon4 |
| 19:41869166_T/A | c.308T > A | Exon4 |
| 19:41869178_T/C | c.320T > G | Exon4 |
| 19:41869185_GC/G | c.328delC | Exon4 |
| 19:41869192_A/ATGG | c.335_337TGG | Exon4 |
| 19:41869198_G/T | c.340G > T | Exon4 |
| 19:41869198_GA/G | c.341delA | Exon4 |
| 19:41869198_G/GAA | c.344_345insAA | Exon4 |
| 19:41869212_T/TG | c.356_356insG | Exon4 |
| 19:41869215_G/A | c.356 + 1G > A | Intron4 |
| 19:41869215_G/T | c.356 + 1G > T | Intron4 |
| 19:41869216_T/A | c.356 + 2T > A | Intron4 |
| 19:41869217_A/C | c.356 + 3A > C | Intron4 |
| 19:41869698_G/A | c.357-1G > A | Intron4 |
| 19:41869698_G/T | c.357-1G > T | Intron4 |
| 19:41869700_G/A | c.358G > A | Exon5 |
| 19:41869708_A/ACT | c.367_368dup | Exon5 |
| 19:41869713_C/CA | c.372_373insA | Exon5 |
| 19:41869718_C/T | c.376C > T | Exon5 |
| 19:41869718_C/CGGACAAAG | c.386_387insCGGACAAAG | Exon5 |
| 19:41869722_G/A | c.380G > A | Exon5 |
| 19:41869724_C/T | c.382C > T | Exon5 |
| 19:41869724_CAA/C | c.384_385delAA | Exon5 |
| 19:41869731_ATC/A | c.390_391delTC | Exon5 |
| 19:41869734_T/C | c.392T > C | Exon5 |
| 19:41869734_T/G | c.392T > G | Exon5 |
| 19:41869742_A/AT | c.401_402insT | Exon5 |
| 19:41869745_G/A | c.403G > A | Exon5 |
| 19:41869748_G/T | c.406G > T | Exon5 |
| 19:41869752_A/G | c.410A > G | Exon5 |
| 19:41869754_G/A | c.411 + 1G > A | Intron5 |
| 19:41869755_T/C | c.411 + 2T > C | Intron5 |
| 19:41871335_CCATCTTTTCCCACAGGTGG/C | c.412-13_417del | Exon6 |
| 19:41871349_AG/A | c.412delG | Exon6 |

-continued

| Mutation position | Transcript Consequence (NM_001022) | NM_001022.4 (RPS19) |
|---|---|---|
| 19:41871351_G/T | c.412G > T | Exon6 |
| 19:41871355_CA/A | c.417delA | Exon6 |
| 19:41871356_AG/A | c.418delG | Exon6 |

CRISPR Nucleases and PAM Recognition

In some embodiments, the sequence specific nuclease is an RNA guided DNA nuclease. In some embodiments, the RNA sequence which guides the RNA guided DNA nuclease binds to and directs the RNA guided DNA nuclease to (1) a sequence comprising at least one nucleotide which differs between a mutant allele and its counterpart functional allele (e.g., SNP or a pathogenic DBA mutation) or (2) to a non-coding region common to both alleles of a gene bearing the pathogenic mutation (i.e., both the functional allele and the allele bearing the pathogenic mutation). In additional embodiments, the RNA sequence which guides the RNA guided DNA nuclease binds to and directs the RNA guided DNA nuclease to a sequence at a distance of up to 1000 basepairs from an edge of an exon bearing a pathogenic mutation. In some embodiments, the CRISPR complex further comprises a tracrRNA. In some embodiments, the sequence specific nuclease is selected from CRISPR nucleases, or functional variants thereof. In a non-limiting example, in which the RNA guided DNA nuclease is a CRISPR protein, the at least one nucleotide which differs between a target allele (e.g., bearing a pathogenic mutation) and the other allele (e.g., bearing a different or the same pathogenic mutation) may be within the PAM site and/or proximal to the PAM site within the region that the RNA molecule is designed to hybridize to. In another non-limiting example, A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the proto-spacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for *Streptococcus pyogenes* Cas9 WT (Sp-CAS9); NNGRRT for *Staphylococcus aureus* (SaCas9); NNNVRYM for *Jejuni* Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

RNA molecules of the present invention are each designed to form complexes in conjunction with one or more different CRISPR nucleases and designed to target polynucleotide sequences of interest utilizing one or more different PAM sequences respective to the CRISPR nuclease utilized. Non-limiting examples of suitable PAM sequences include NGG, NGAN, NGNG, NGAG, NGCG, NNGRRT, NNNNGATT, TTTV, NNNVRYM, NRTAM, NAG, NNYAAT, NRTAM, NRRAR, NGGNR, NRTAH, NGGNG, and NRRWC.

In some embodiments, an RNA-guided DNA nuclease e.g., a CRISPR nuclease, may be used to induce a double-strand DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015-0211023, incorporated herein by reference.

CRISPR systems that may be used in the practice of the invention vary greatly. CRISPR systems can be a type I, a type II, type III or Type V system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas12a, Cas12b, Cas12c, Cas12d, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966 (See Koonin 2017).

In some embodiments, the RNA-guided DNA nuclease is a CRISPR nuclease derived from a type II CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium dificile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia*

*spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Francisella* cf. *novicida* Fx1, *Alicyclobacillus acidoterrestris, Oleiphilus* sp., Bacterium CG09_39_24, Deltaproteobacteria bacterium, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., spCas9 D1135E variant, spCas9 VQR variant, spCas9 EQR variant, or spCas9 VRER variant may also be used in the context of the invention.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from Acidaminococcus and Lachnospiraceae have been shown to carry out efficient genome-editing activity in human cells. (See Zetsche et al. (2015) Cell.).

In some embodiments, the CRISPR nuclease comprises one or more nuclear localization sequences (NLS), cell penetrating peptide sequences, and/or affinity tags. The NLS may be fused to the CRISPR nuclease or may be an in internal NLS. In an embodiment, the CRISPR nuclease comprises one or more nuclear localization sequences of sufficient strength to drive accumulation of a CRISPR complex comprising the CRISPR nuclease in a detectable amount in the nucleus of a eukaryotic cell.

Thus, an RNA guided DNA nuclease of a Type II CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to one or more of: modified bases, modified sugar moieties, or modified inter-nucleoside linkages. Non-limiting examples of suitable chemical modifications include: 4-acetyleytidine, 5-(carboxyhydroxymethyl)uridine, 2'-O-methylcytidine, 5-carboxymethylaninomethyl-2-thiouridine, 5-carboxvmethylaminomethy luridine, dihydrouridine, 2'-O-nethylpseudouridine, "beta, D-galactosylqueuosine", 2'-O-methylguanosine, inosine, N6-isopentenyladenosine, 1-methyladenosine, 1-methylpseudouridine, 1-methylguanosine, 1-methylinosine, "2,2-dimethylguanosine", 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, "beta, D-mannosylqueuosine", 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl)N-methylcarbanoyl)threonine, uridine-5-oxyacetic acid-methylester, uridine-5-oxyacetic acid, wybutoxosine, queuosine, 2-thiocytidine, 5-methyl-2-thiouridine, 2-thiouridine, 4-thiouridine, 5-methyluridine, N-((9-beta-D-ribofuranosylpurine-6-yl)-carbamoyl)threonine, 2'-O-methyl-5-methyluridine, 2'-O-methyluridine, wybutosine, "3-(3-amino-3-carboxy-propyl)uridine, (acp3) u", 2'-0-methyl (M), 3'-phosphorothioate (MS), 3'-thioPACE (MSP), pseudouridine, or 1-methyl pseudo-uridine. Each possibility represents a separate embodiment of the present invention.

Further non-limiting examples of suitable chemical modifications include: $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); miG (1-methylguanosine); $m^2G$ ($N^2$-methylguanosine); $m^7G$ (7-methylguanosine); Gm (2'-O-methylguanosine); $m^2$ 2G ($N^2,N^2$-dimethylguanosine); $m^2Gm$ ($N^2$'2'-O-dimethylguanosine); $m^2$ 2Gm ($N^2,N^2$, 2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); G (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $nCm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmmm^5s^2U$ (5-carboxymethylaminomethyl-2-thiouridine); dimethyladenosine); Im (2'-O-methylinosine); $m^4C$ ($N^4$-methylcytidine); $m^4Cm$ ($N^4,2'$-O-dimethylcytidine); $hm^5C$ (5-hydroxymethylcytidine); $m^3U$ (3-methyluridine); $cm^5U$ (5-carboxymethyluridine); $m^6Am$ ($N^6,2'$-O-dimethyladenosine); $m^6 2Am$ ($N^6,N^6,$O-2'-trimethyladenosine); $m^{2'}7G$ ($N^2$,7-dimethylguanosine); m2,2,7G ($N^2,N^2$ 7-trimethylguanosine); $m^3Um$ (3,2'-O-dimethyluridine); $m^5D$ (5-methyldihydrouridine); $f^5Cm$ (5-formyl-2'-O-methylcytidine); $m^1 Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine). Each possibility represents a separate embodiment of the present invention. (See e.g. U.S. Pat. No. 9,750,824).

Delivery to Cells

It is understood that in the methods embodied, the RNA molecules and compositions described herein may be delivered to a target cell or subject by any suitable means. The following embodiments provide non-limiting examples of methods of delivery of the RNA molecules and composition of the present invention.

In some embodiments, RNA molecule compositions of the present invention may be targeted to any cell which contains and/or expresses a mutant allele or a dominant negative allele, including any mammalian or plant cell. For example, in one embodiment the RNA molecule specifically targets a mutated RPS19 allele and the target cell is an HSC. The delivery to the cell may be performed in-vitro, ex-vivo, or in-vivo. Further, the nucleic acid compositions described herein may be delivered as one or more of DNA molecules, RNA molecules, Ribonucleoproteins (RNP), nucleic acid vectors, or any combination thereof. In another example, the RNA molecule targets non-coding region common to both alleles of the RPS19 gene and up to 250 base pairs from an exon bearing a pathogenic mutation position of interest. In such a scenario, a double-strand break is induced in the non-coding region of both alleles, and the mutation of interest can be corrected by DNA repair pathway (e.g. HDR).

In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thio-PACE (MSP), pseudouridine, and 1-methyl pseudo-uridine. Each possibility represents a separate embodiment of the present invention.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Felgner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, *Sinorhizoboium meliloti, Mesorhizobium loti*, tobacco mosaic virus, potato virus X, cauliflower mosaic virus and cassava vein mosaic virus). (See, e.g., Chung et al. (2006) Trends Plant Sci. 11(1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. Nos. 5,049,386, 4,946,787; and 4,897,355, and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186, 183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchschacher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al. (1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various cell types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), perC6 cells, any plant cell (differentiated or undifferentiated), as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and lad (differentiated antigen presenting cells) (as a non-limiting example see Inaba et al. (1992) J. Exp. Med. 176:1693-1702). Stem cells that have been modified may also be used in some embodiments.

Typically, the cells are administered in a pharmaceutical composition comprising at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically-acceptable material, composition or vehicle, such as a liquid or solid filler, diluent, excipient, or solvent encapsulating material.

Any one of the RNA molecule compositions described herein is suitable for genome editing in either mitotic cells or post-mitotic cells or any cell which is not actively dividing, e.g., arrested cells. Examples of post-mitotic cells which may be edited using an RNA molecule composition of the present invention include, but are not limited to, a hepatocyte cell.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via IV injection.

Vectors suitable for introduction of transgenes into immune cells (e.g., T-cells) include non-integrating lentivirus vectors. See, e.g., U.S. Patent Publication No. 2009-0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to/associates with and/or directs the RNA guided DNA nuclease (E.G., CRISPR nuclease) to a sequence comprising at least one nucleotide which differs between a mutant allele and a functional allele (e.g., SNP, disease associated mutation) of a gene of interest (i.e., a sequence of the mutant allele which is not present in the functional allele, a sequence of one of the mutant alleles which is not present in the other mutant allele) or a sequence common to two mutant alleles of a gene of interest. The sequence may be within the disease associated mutation. The sequence may be upstream or downstream to the disease associated mutation. Any sequence difference between a mutant allele and the functional allele may be targeted by an RNA molecule of the present invention to inactivate the mutant allele, or otherwise disable its dominant disease-causing effects, while preserving the activity of the functional allele. In additional embodiments, there is provided an RNA molecule which binds to/associates with and/or directs the RNA guided DNA nuclease to a sequence in a non-coding region upstream or downstream to an exon baring a disease associated mutation.

The disclosed compositions and methods may also be used in the manufacture of a medicament for treating dominant genetic disorders in a patient.

Guide Sequences which Specifically Target a Mutant Allele

A given gene may contain thousands of SNPs. Utilizing a 24 base pair target window for targeting each SNP in a gene would require hundreds of thousands of guide sequences. Any given guide sequence when utilized to target a SNP may result in degradation of the guide sequence, limited activity, no activity, or off-target effects. Accordingly, suitable guide sequences are necessary for targeting a given gene. By on aspect of the present invention, a novel set of guide sequences have been identified for repairing/correcting/modifying a mutant allele of RPS19 gene to treat/ameliorate/prevent DBA.

One aspect of the present disclosure provides guide sequences capable of specifically targeting a mutant allele while leaving a second allele (e.g., functional allele) unmodified. The guide sequences of the present invention are designed to, and are most likely to, specifically differentiate between a mutant allele and a functional allele. Of all possible guide sequences which target a mutant allele desired to be edited/corrected/modified/repaired, the specific guide sequences disclosed herein are specifically effective to function with the disclosed embodiments.

The present disclosure also provides guide sequences capable of specifically targeting a mutant allele. Of all possible guide sequences which target the mutant allele desired to be edited/corrected/modified/repaired, the specific guide sequences disclosed herein are specifically effective to function with the disclosed embodiments.

Briefly, the guide sequences may have properties as follows: (1) targets a SNP/insertion/deletion/indel with a prevalence of heterozygosity in the general population, in a specific ethnic population, or in a patient population above 1% or 10%; (2) targets a location of a SNP/insertion/deletion/indel proximal to a portion of the gene e.g., within 250 base pairs of a mutation or exon of the gene; and (3) targets a mutant allele which by targeting a founder or common pathogenic mutation for the disease/gene. In some embodiments, the SNP/insertion/deletion/indel heterozygosity rate in a population of interest is above 1%, 2%, 3%, 4%, 5%, 6%, 7%, 8%, 9%, 10%, 11%, 12%, 13%, 14%, or 15%. Each possibility represents a separate embodiment and may be combined at will.

Guide sequences of the present invention may target a SNP position in a distance of less than 2000 nucleotides, 1000 nucleotides, 500 nucleotides, 400 nucleotides, 300 nucleotides, 250 nucleotides, 200 nucleotides, 100 nucleotides from the disease-associated mutation, or within the disease associated mutation. Each possibility represents a separate embodiment.

Guide sequences of the present invention also may: (1) target a heterozygous sequence in a SNP position for the targeted gene; (2) target a SNP position with a prevalence of the SNP/insertion/deletion/indel in the general population, in a specific ethnic population, or in a patient population above 1% or 10%; (3) have a guanine-cytosine content of greater than 30% and less than 85%; (4) have no repeats of seven or more thymine/uracil, guanine, cytosine, or adenine residues; (6) have no off-target of zero mismatches in the genome identified by off-target analysis.

The at least one nucleotide which differs between the mutant allele and the second allele (e.g., functional/wild type allele), may be upstream, downstream or within the sequence of the disease-causing mutation of the gene of interest. The at least one nucleotide which differs between the mutant allele and the second allele, may be within an exon or within an intron of the gene of interest.

In some embodiments, the at least one nucleotide is a single nucleotide polymorphism (SNP). In some embodiments, each of the nucleotide variants of the SNP may be expressed in the mutant allele (REF/SNP) and targeted by a guide sequence. In some embodiments, the SNP may be a founder or common pathogenic mutation.

In some embodiments, the at least one nucleotide which differs between the mutant allele and the functional allele is linked to/co-exists with the disease-causing mutation in high prevalence in a population. In such embodiments, "high prevalence" refers to at least 92%, 93%, 94%, 95%, 96%, 97%, 98%, 99%, or 100%. Each possibility represents a separate embodiment of the present invention. In one embodiment, the at least one nucleotide which differs between the mutant allele and the functional allele, is a disease-associated mutation.

Guide sequences of the present invention may satisfy any one of the above criteria and are most likely to differentiate between a mutant allele from its corresponding functional allele.

In some embodiments, the RNA molecule targets a SNP/REF sequence linked to a SNP position, such as in a non-limiting example: 19:41869228_A_G, 19:41869228_A_G, 19:41869823_T_C, rs1385169206, rs2075749, rs2075750, rs2075754. SNP ID NOs are based on NCBI's 2018 database of Single Nucleotide Polymorphisms (dbSNP). For variants with no available rs number, variant characteristics are indicated based on gnomAD v3 database and UCSC Genome Browser assembly ID: hg38, sequencing/assembly provider ID: Genome reference consortium Human GRCh38.p12 (GCA_00001405.27) Assembly date December 2013 initial release December 2017 patch release 12)).

Strategies for HDR repair of a pathogenic mutation associated with DBA may involve a guide sequence targeting the pathogenic mutation itself or alternatively a guide sequence targeting a SNP located upstream or downstream to the mutation to mediate a DSB in proximity to the mutation. The strategies may further include a sequence repair/correction step by utilizing a donor/template sequence that (e.g., a single-stranded donor oligonucleotides (ssODN), double-stranded Donor (PCR product), Minicircle or virus (rAAV or Lentivirus)). In some embodiments, a DSB is affected in a non-coding region of both alleles of a gene, and a donor template for HDR overlaps in sequence complementarity with an entire exon in which a pathogenic mutation is located.

In an exemplary strategy, a mutant allele bearing a disease associated mutation, such as rs104894711 (p.Arg62Trp c.184C>T) in exon 4 of chromosome 19, is targeted by guide sequences designed to target the disease-associated mutation itself. Non-limiting examples of such guide sequences are listed in Table 2.

In some embodiments, a mutant allele bearing a mutation is targeted by guide sequences designed to target SNP positions located up to 50, 100, 200, 500, 1000, 1500, 2000 bases from the pathogenic mutation. Each possibility represents a separate embodiment. Non-limiting examples of suitable guide sequences are indicated in Table 2.

In an exemplary strategy, a mutant allele bearing a mutation in exon 2 may be targeted by guide sequences designed to target a SNP position located in intron 2, such as rs1385169206 and rs2075749, or s SNP position located in intron 1, such as 19:41860325_C_T. Non-limiting examples of such guide sequences are indicated in Table 2. In another exemplary strategy, a mutant allele bearing a mutation in exon 3 may be targeted by guide sequences designed to target a SNP position located in intron 2, such as rs1385169206 and rs2075749, or a SNP position located in intron 3. Non-limiting examples of such guide sequences are indicated in Table 2. In another exemplary strategy, a mutant allele bearing a mutation in exon 4 or 5 may be targeted by guide sequences designed to target a SNP position located in intron 4, such as 19:41869228_A_G, and rs2075750. Non-limiting examples of such guide sequences are indicated in Table 2. In another exemplary strategy, a mutant allele bearing a mutation in exon 5 may be targeted by guide sequences designed to target a SNP position located in intron 5, such as rs2075754 and 19:41869823_T_C. Non-limiting examples of such guide sequences are indicated in Table 2.

Although a large number of guide sequences can be designed to target a mutant allele, a subset within the sequences identified by SEQ ID NOs: 1-20465 disclosed herein were specifically selected to effectively implement the methods set forth herein and to effectively discriminate between alleles.

A subset of guide sequences for use as described in the embodiments herein were designed to associate with different SNPs or mutations within a sequence of a mutated RPS19 allele. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1 (PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized.

Guide Sequences which Target a Sequence within a Non-Coding Region in a Proximity to an Exon Bearing a Pathogenic Mutation The present disclosure also provides guide sequences capable of specifically targeting a CRISPR nuclease to induce a DSB at a location that is 500, 250, or fewer nucleotides from the first or the last nucleotide of a coding region of the RPS19 gene containing the mutation associated with DBA desired to be edited/corrected/modified/repaired. The specific guide sequences disclosed herein are specifically effective to function with the disclosed embodiments.

Strategies for HDR repair of a pathogenic mutation associated with DBA may involve a guide sequence targeting a sequence within a non-coding region of the gene, in a distance of up to 1000, 500, 250, or fewer nucleotides from the first or the last nucleotide of a coding region of the RPS19 gene containing the mutation associated with DBA desired to be edited/corrected/modified/repaired. The strategies may further include a sequence repair/correction step by utilizing a donor/template sequence that (e.g., a single-stranded donor oligonucleotides (ssODN), double-stranded Donor (PCR product), Minicircle or virus (rAAV or Lentivirus)). In some embodiments, the donor/template sequence comprises a sequence complimentary to a region extending from the position of the DSB to a pathogenic mutation. In such embodiments, the donor/template sequence further comprises homology arms flanking the site of the DSB and the pathogenic mutation. In some embodiments, the donor/template sequence comprises a sequence complimentary to a region comprising an entire exon. In some embodiments, the exon containing the pathogenic mutation, or a portion thereof which contains the pathogenic mutation, is corrected or replaced to remove the pathogenic mutation.

In some embodiments, a mutant allele bearing a mutation and functional allele are targeted by guide sequences designed to target a sequences located in a non-coding region up to 50, 100, 200, 300, 400, 500, 600, 700, 800, 900, 1000, bases from an edge of a coding region bearing the pathogenic mutation. Each possibility represents a separate embodiment. Non-limiting examples of suitable guide sequences that associate with different sequences in a non-coding region of a RPS19 gene are indicated in Table 2.

In an exemplary strategy, a mutation in exon 1 may be targeted by guide sequences designed to target a sequence common to both alleles of a gene located up to 250 basepairs from exon 1 (Upstream_Exon_1) or located in intron 1 up to 250 basepairs from exon 1 (Downstream_Exon_1). In an exemplary strategy, a mutation in exon 2 may be targeted by guide sequences designed to target a sequence common to both alleles of a gene located in intron 1 up to 250 basepairs from exon 2 (Upstream_Exon_2) or intron 2 up to 250 basepairs from exon 2 (Downstream_Exon_2). In an exemplary strategy, a mutation in exon 3 may be targeted by guide sequences designed to target a sequence common to both alleles of a gene located in intron 2 up to 250 basepairs from the exon (Upstream_Exon_3) or in intron 3 up to 250 basepairs from the exon (Downstream_Exon_3). In an exemplary strategy, a mutation in exon 4 may be targeted by guide sequences designed to target a sequence common to both alleles of a gene located in intron 3 up to 250 basepairs from the exon (Upstream_Exon_4) or in intron 4 up to 250 basepairs from the exon (Downstream_Exon_4). In an exemplary strategy, a mutation in exon 5 may be targeted by guide sequences designed to target a sequence common to both alleles of a gene located in intron 4 up to 250 basepairs from the exon (Upstream_Exon_5) or in intron 5 up to 250 basepairs from the exon (Downstream_Exon_5). Non-limiting examples of suitable guide sequences for the exemplary strategies are indicated in Table 2.

In the present invention, a novel set of guide sequences have been identified for repairing/correcting/modifying a mutant allele of RPS19 gene to treat, ameliorate, or prevent DBA.

TABLE 2

Guide sequences designed for use as described in the embodiments herein. Each engineered guide molecule is further designed such as to associate with a target genomic DNA sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| 19:41859951_T_C | 1-46 | 47-94 | 95-144 |
| 19:41860011_C_T | 145-190 | 191-238 | 239-288 |
| 19:41860139_G_T | 289-334 | 335-382 | 383-432 |
| 19:41860151_C_T | 433-478 | 479-526 | 527-576 |
| 19:41860216_C_T | 577-622 | 623-670 | 671-720 |
| 19:41860280_A_G | 721-743 | 744-752 | 753-765 |
| 19:41860303_C_T | 766-810 | 811-853 | 854-899 |
| 19:41860766_C_A | 900-945 | 946-993 | 994-1043 |
| 19:41860768_C_T | 906, 929-930, 940, 1044-1085 | 952, 958, 965, 988, 1086-1129 | 995, 1007, 1011, 1014, 1130-1175 |
| 19:41860777_G_T | 1176-1221 | 1222-1269 | 1270-1319 |
| 19:41860817_G_T | 1320-1365 | 1366-1413 | 1414-1463 |
| 19:41860823_G_C | 1464-1509 | 1510-1557 | 1558-1607 |
| 19:41860842_A_G | 1608-1653 | 1654-1701 | 1702-1751 |
| 19:41860853_TG_T | 1752-1797 | 1798-1845 | 1846-1895 |
| 19:41861111_G_A | 1896-1941 | 1942-1989 | 1990-2039 |
| 19:41861138_G_A | 2040-2085 | 2086-2133 | 2134-2183 |
| 19:41861144_A_AT | 2184-2231 | 2232-2281 | 2282-2333 |
| 19:41861166_CAA_C | 2219, 2228, 2334-2377 | 2268, 2277, 2378-2423 | 2320, 2329, 2424-2471 |

TABLE 2-continued

Guide sequences designed for use as described in the embodiments herein. Each engineered
guide molecule is further designed such as to associate with a target genomic DNA
sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| 19:41861179_C_T | 2472-2517 | 2518-2565 | 2566-2615 |
| 19:41861204_C_T | 2616-2661 | 2662-2709 | 2710-2759 |
| 19:41861217_G_C | 2760-2805 | 2806-2853 | 2854-2903 |
| 19:41869029_A_G | 2904-2949 | 2950-2993 | 2994-3041 |
| 19:41869033_TC_CT | 3042-3087 | 3088-3135 | 3136-3185 |
| 19:41869036_A_C | 3065, 3069, 3186-3229 | 3106, 3121, 3230-3271 | 3152, 3157, 3272-3317 |
| 19:41869042_C_T | 3318-3363 | 3364-3411 | 3412-3461 |
| 19:41869043_G_A | 3322, 3328, 3335, 3346, 3349, 3360, 3462-3501 | 3369, 3377, 3382, 3391, 3394, 3397, 3502-3543 | 3412, 3417, 3426, 3440, 3446, 3448, 3544-3587 |
| 19:41869066_G_A | 3588-3633 | 3634-3681 | 3682-3731 |
| 19:41869108_A_T | 3732-3777 | 3778-3825 | 3826-3875 |
| 19:41869138_C_T | 3876-3921 | 3922-3969 | 3970-4019 |
| 19:41869140_A_AGG | 3895, 3907, 3911-3912, 4020-4065 | 3941, 3953, 3958, 3960, 4066-4113 | 3989, 3991, 4003, 4008, 4114-4163 |
| 19:41869151 GTGTG GTGTGTG | 4164-4213 | 4214-4264 | 4265-4318 |
| 19:41869152_T_TTG | 4172, 4181, 4191, 4208, 4213, 4319-4363 | 4220, 4232, 4242, 4258, 4263, 4364-4403 | 4271, 4282, 4294, 4312, 4317, 4404-4448 |
| 19:41869162_CG_C | 4040, 4043, 4050, 4056, 4059, 4449-4489 | 4087, 4090, 4097, 4103, 4106, 4490-4528 | 3989, 4135, 4145, 4151, 4154, 4529-4571 |
| 19:41869166_T_A | 4458, 4467, 4473, 4484, 4572-4613 | 4103, 4493, 4510, 4523, 4614-4649 | 4151, 4154, 4538, 4551, 4650-4691 |
| 19:41869192_A_ATGG | 4692-4743 | 4744-4797 | 4798-4853 |
| 19:41869217_A_C | 4727, 4729, 4854-4897 | 4781, 4783, 4792, 4898-4942 | 4837, 4839, 4848, 4943-4989 |
| 19:41869708_A_ACT | 4990-5039 | 5040-5091 | 5092-5145 |
| 19:41869722_G_A | 5146-5191 | 5192-5239 | 5240-5289 |
| 19:41869724_CAA_C | 5160, 5175, 5290-5333 | 5221, 5225, 5334-5379 | 5259, 5274, 5380-5427 |
| 19:41869724_C_T | 5160, 5162, 5173, 5175, 5308, 5319-5320, 5322, 5428-5465 | 5208, 5221-5222, 5225, 5349, 5353-5354, 5367, 5466-5505 | 5259, 5271, 5274-5275, 5395-5396, 5400, 5411, 5506-5547 |
| 19:41869748_G_T | 5548-5593 | 5594-5641 | 5642-5691 |
| 19:41869752_A_G | 5692-5737 | 5738-5785 | 5786-5835 |
| 19:41869755_T_C | 5710, 5735, 5836-5879 | 5750, 5758, 5880-5925 | 5809, 5824, 5926-5973 |
| 19:41860325_C_T | 5974-5977, 5977-5981, 5981-5983, 5983-5989, 5989-5991, 5991-5997, 5997-6000, 6000-6003, 6003-6009 | 6010-6011, 6011-6015, 6015-6017, 6017-6020 | 6021-6022, 6022-6027, 6027-6032, 6032-6036, 6036-6038, 6038-6041 |
| 19:41869228_A_G | 4858, 4864, 4882, 4894, 6042, 6042-6044, 6044-6045, 6045-6055, 6055-6060, 6060-6070, 6070-6079, 6079-6088, 6088-6093 | 4902, 4908, 4911, 4939, 6094-6097, 6097-6109, 6109-6113, 6113-6123, 6123-6126, 6126-6133, 6133-6134, 6134-6142, 6142-6147 | 4947, 4953, 4957, 4982, 6148-6151, 6151-6158, 6158-6168, 6168-6178, 6178-6181, 6181-6188, 6188-6189, 6189-6190, 6190-6203 |
| 19:41869823_T_C | 6204-6208, 6208-6211, 6211-6222, 6222-6223, 6223-6226, 6226-6240, 6240-6258, 6258-6261, 6261-6287 | 6288-6292, 6292-6295, 6295-6306, 6306-6307, 6307-6323, 6323-6345, 6345-6348, 6348-6349, 6349-6375 | 6376-6380, 6380-6395, 6395-6396, 6396-6397, 6397-6413, 6413-6420, 6420-6436, 6436-6439, 6439-6467 |
| rs1385169206 | 6468, 6468-6469, 6469-6474, 6474-6481, 6481-6482, 6482-6510, 6510-6513, 6513-6514, 6514-6517, 6517-6524, 6524-6536, 6536-6537, 6537-6547 | 6548, 6548-6555, 6555-6562, 6562-6563, 6563-6570, 6570-6571, 6571-6591, 6591-6594, 6594-6595, 6595-6602, 6602-6614, 6614-6615, 6615-6625 | 6626-6642, 6642-6643, 6643-6650, 6650-6651, 6651-6656, 6656-6657, 6657-6675, 6675-6678, 6678-6679, 6679-6688, 6688-6700, 6700-6701, 6701-6711 |
| rs2075749 | 6468-6469, 6471, 6473, 6476, 6479, 6479, 6482, 6484, 6489, 6498, 6501, | 6548, 6550, 6552, 6554, 6557, 6560, 6560, 6563, 6565, 6568, 6568, 6571, | 6627, 6629, 6631, 6633, 6637, 6640, 6640, 6643, 6645, 6648, 6648, 6651, |

TABLE 2-continued

Guide sequences designed for use as described in the embodiments herein. Each engineered
guide molecule is further designed such as to associate with a target genomic DNA
sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| | 6505-6506, 6509, 6518, 6521, 6526, 6528, 6530, 6530, 6532, 6532, 6535, 6540, 6542, 6542, 6544, 6546, 6712-6716, 6716-6724, 6724-6739, 6739-6753, 6753-6770 | 6576, 6586-6587, 6590, 6604, 6606, 6608, 6608, 6610, 6613, 6618, 6620, 6620, 6622, 6624, 6771-6775, 6775-6783, 6783-6787, 6787-6796, 6796-6827 | 6654, 6654, 6657, 6660, 6663, 6666, 6670-6671, 6674, 6690, 6692, 6694, 6694, 6696, 6699, 6704, 6706, 6708, 6710, 6828-6832, 6832-6840, 6840-6844, 6844-6864, 6864-6888 |
| rs2075750 | 6889-6892, 6892-6914, 6914-6918, 6918-6930, 6930-6941, 6941-6961, 6961-6962, 6962-6970, 6970-6972 | 6973-6976, 6976-6998, 6998-7004, 7004-7006, 7006-7017, 7017-7028, 7028-7050, 7050-7058, 7058-7060 | 7061-7064, 7064-7080, 7080-7087, 7087-7093, 7093-7095, 7095-7112, 7112-7119, 7119-7141, 7141-7152 |
| rs2075754 | 7153-7171, 7171-7178, 7178-7181, 7181-7185, 7185-7210, 7210-7216, 7216-7226, 7226-7236, 7236 | 7237-7255, 7255-7262, 7262-7265, 7265-7267, 7267-7296, 7296-7302, 7302-7312, 7312-7318, 7318-7324 | 7325-7351, 7351-7354, 7354-7356, 7356-7357, 7357-7373, 7373-7394, 7394-7404, 7404-7410, 7410-7416 |
| Downstream_Exon_1 | 777, 786, 792, 5977, 5989, 5997, 6000, 6009, 7417-7770 | 6011, 6015, 7771-8050 | 6022, 6032, 6038, 8051-8345 |
| Downstream_Exon_2 | 1757, 1765, 1770-1771, 6468-6469, 6471, 6473, 6476, 6478, 6482, 6484, 6486, 6489, 6491, 6501, 6503, 6505, 6509, 6512-6513, 6516, 6521, 6523- | 1803, 1811, 1815, 1817, 6548, 6550, 6552, 6554, 6557, 6559, 6563, 6565, 6567, 6571, 6573, 6576, 6584, 6586, 6590, 6593-6594, 6597, 6601-6603, | 1851, 1859, 1863, 1885, 6627, 6629, 6631, 6633, 6637, 6639, 6643, 6645, 6647, 6651, 6653, 6657, 6660, 6666, 6668, 6670, 6674, 6677-6678, 6681, |
| Downstream_Exon_2 | 6525, 6535, 6539, 6716, 6719, 6724, 6729, 6731, 6739, 6745, 6749, 6753, 6757, 8346-8757 | 6613, 6617, 6775, 6778, 6783, 6787, 6790, 6796, 6802, 6806, 6809, 6813, 8758-9163 | 6687-6689, 6699, 6703, 6832, 6835, 6840, 6844, 6855, 6861, 6864, 6866, 6869, 6873, 9164-9568 |
| Downstream_Exon_3 | 2775, 2782, 2797, 2800, 6468-6469, 6471, 6473, 6476, 6478, 6482, 6484, 6486, 6489, 6491, 6501, 6503, 6505, 6509, 6512-6513, 6516, 6521, 6523-6525, 6535, 6539, 6716, 6719, 6724, 6729, 6731, 6739, 6745, 6749, 6753, 6757, 8346-8347, 8349-8352, 8354-8356, 8358, 8360, 8363-8365, 8367, 8369-8370, 8372, 8375-8381, 8383, 8385, 8389, 8392-8393, 8396, 8399, 8404-8405, 8407, 8412, 8415-8418, 8421-8422, 8427, 8430-8431, 8433-8434, 8436, 8438-8440, 8444-8447, 8449-8454, 8456, 8459-8460, 8462-8464, 8468-8469, 8474, 8477-8478, 8481-8482, 8484-8485, 8487, 8489, 8491, 8493, 8496, | 2828-2829, 2845, 2848, 6548, 6550, 6552, 6554, 6557, 6559, 6563, 6565, 6567, 6571, 6573, 6576, 6584, 6586, 6590, 6593-6594, 6597, 6601-6603, 6613, 6617, 6775, 6778, 6783, 6787, 6790, 6796, 6802, 6806, 6809, 6813, 8758-8759, 8761-8764, 8766-8768, 8770, 8772, 8775-8777, 8779, 8781-8782, 8784, 8787-8793, 8795, 8801, 8804-8805, 8808, 8810, 8815-8816, 8818, 8823, 8826-8829, 8832-8833, 8838, 8840-8841, 8843-8844, 8846, 8848-8850, 8854-8857, 8859-8864, 8866, 8869-8870, 8872-8874, 8878-8879, 8884, 8887-8888, 8891-8892, 8894-8895, 8897, 8899, 8901, 8903, 8907, 8909-8911, | 2861, 2878-2879, 2898, 6627, 6629, 6631, 6633, 6637, 6639, 6643, 6645, 6647, 6651, 6653, 6657, 6660, 6666, 6668, 6670, 6674, 6677-6678, 6681, 6687-6689, 6699, 6703, 6832, 6835, 6840, 6844, 6855, 6861, 6864, 6866, 6869, 6873, 9164-9165, 9167-9170, 9172-9174, 9176, 9178, 9181-9183, 9185, 9187-9188, 9190, 9193-9199, 9201, 9207, 9210-9211, 9214, 9216, 9221-9222, 9224, 9229, 9232-9235, 9238-9239, 9244, 9246-9247, 9249-9250, 9252, 9254-9256, 9260-9263, 9265-9270, 9272, 9275-9276, 9278-9280, 9284-9285, 9290, 9293-9294, 9297-9298, 9300-9301, 9303, 9305, 9307, 9309, 9313, |

TABLE 2-continued

Guide sequences designed for use as described in the embodiments herein. Each engineered
guide molecule is further designed such as to associate with a target genomic DNA
sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| | 8499, 8501-8503, | 8916-8917, 8920, | 9315-9317, 9322- |
| | 8508-8509, 8512, | 8924, 8929-8930, | 9323, 9326, 9330, |
| | 8516, 8521-8522, | 8934-8935, 8942- | 9336-9337, 9341- |
| | 8526-8527, 8533- | 8943, 8945, 8952, | 9342, 9349-9350, |
| | 8534, 8536, 8543, | 8955, 8960-8961, | 9352, 9359, 9362, |
| | 8546, 8551-8552, | 8963, 8975-8977, | 9367-9368, 9370, |
| | 8554, 8566-8568, | 8979-8981, 8984, | 9382-9384, 9386- |
| | 8570-8572, 8575, | 8989, 8995, 8998- | 9388, 9391, 9396, |
| Downstream_Exon_3 | 8580, 8586, 8589- | 8999, 9003-9004, | 9402, 9405-9406, |
| | 8590, 8594-8595, | 9006, 9008, 9010, | 9410-9411, 9413, |
| | 8597, 8599, 8601, | 9017, 9019, 9023, | 9415, 9424, 9426, |
| | 8608, 8610, 8614, | 9025, 9027-9030, | 9429, 9431, 9433- |
| | 8616, 8618-8621, | 9034, 9038-9040, | 9436, 9440, 9444- |
| | 8625, 8629-8631, | 9042, 9045-9046, | 9445, 9447, 9451, |
| | 8633, 8637-8638, | 9050, 9055, 9059- | 9452, 9456, 9461, |
| | 8642, 8647, 8651- | 9064, 9067, 9070, | 9465-9470, 9473, |
| | 8656, 8659, 8662, | 9072-9073, 9076, | 9476, 9478-9479, |
| | 8664-8665, 8668, | 9079-9080, 9083- | 9482, 9485-9486, |
| | 8671-8672, 8675- | 9084, 9086-9088, | 9489-9490, 9492- |
| | 8676, 8678-8679, | 9092, 9095, 9099, | 9493, 9495, 9499, |
| | 8681, 8685, 8688, | 9106-9107, 9110- | 9502, 9506, 9513- |
| | 8692, 8699-8700, | 9112, 9116-9120, | 9514, 9517-9519, |
| | 8703-8705, 8709- | 9123, 9125, 9132, | 9523-9527, 9529, |
| | 8713, 8716, 8718, | 9136, 9142-9143, | 9531, 9538, 9542, |
| | 8725, 8729, 8735- | 9146-9147, 9150- | 9548-9549, 9552- |
| | 8736, 8739-8740, | 9151, 9155, 9158, | 9553, 9556-9557, |
| | 8743-8744, 8748, | 9803-10028 | 9561, 9564, |
| | 8751, 9569-9802 | | 10029-10256 |
| Downstream_Exon_4 | 4858, 4864, 4894, | 4902, 4908, 4911, | 4947, 4957, 4982, |
| | 6045, 6052, 6056, | 6099, 6106, 6112, | 6152, 6158, 6160, |
| | 6059, 6061, 6070, | 6114, 6123-6124, | 6167, 6169, 6178- |
| | 6072, 6079, 6088, | 6133-6134, 6142, | 6179, 6188, 6190, |
| | 6090-6091, | 6144-6145, 10678- | 6199, 6201, |
| | 10257-10677 | 11081 | 11082-11490 |
| Downstream_Exon_5 | 5856, 5869, 6206, | 5888, 5914, 6290, | 5934, 5942, 6378, |
| | 6211-6212, 6214, | 6295-6296, 6298, | 6383, 6385, 6387, |
| | 6216-6217, 6222, | 6300-6301, 6306, | 6389-6390, 6395- |
| | 6226-6227, 6229, | 6310, 6312, 6314, | 6396, 6400, 6402, |
| | 6237, 6247, 6250, | 6322, 6334, 6337, | 6404, 6412, 6425, |
| | 6252, 6256, 6258- | 6339, 6343, 6345- | 6428, 6430, 6434, |
| | 6259, 6264, 6266, | 6346, 6348, 6352, | 6436-6437, 6439, |
| | 6268, 6270, 6277, | 6354, 6356, 6358, | 6444, 6446, 6448, |
| | 6279, 6889-6890, | 6365, 6367, 6973- | 6450, 6457, 6459, |
| | 6894, 6896, 6900, | 6974, 6978, 6980, | 7061-7062, 7066, |
| | 6902, 6906, 6910, | 6984, 6986, 6990, | 7068, 7072, 7074, |
| | 6914-6915, 6920, | 6994, 6998-6999, | 7078, 7080, 7083, |
| | 6924, 6930-6931, | 7001, 7007, 7011, | 7087-7088, 7090, |
| | 6941-6942, 6948, | 7017-7018, 7028- | 7096, 7100, 7106, |
| | 6952, 6954, 6957, | 7029, 7035, 7039, | 7108, 7119-7120, |
| | 6962, 6965, 6967, | 7041, 7044, 7050, | 7126, 7130, 7132, |
| | 11491-11893 | 7053, 7055, | 7135, 7141, 7144, |
| | | 11894-12290 | 7146, 12291- |
| | | | 12685 |
| Downstream_Exon_6 | 7153, 7155, 7157, | 7237, 7239, 7241, | 7325, 7327, 7329, |
| | 7160, 7165, 7168, | 7244, 7249, 7252, | 7332, 7337, 7340, |
| Downstream_Exon_6 | 7171-7172, 7176, | 7255-7256, 7260, | 7343, 7345, 7349, |
| | 7178, 7181, 7188, | 7262, 7265, 7267, | 7351, 7354, 7356- |
| | 7193, 7199, 7202, | 7274, 7279, 7285, | 7357, 7364, 7369, |
| | 7207, 7211, 7217, | 7288, 7293, 7297, | 7376, 7379, 7384, |
| | 7219, 7225, 7227, | 7303, 7305, 7311, | 7389, 7395, 7397, |
| | 7232, 7236, | 7313, 7319, 7323, | 7403, 7405, 7411, |
| | 12686-12849, | 13108-13518 | 7415, 13519- |
| | 12849-13107 | | 13934 |
| Upstream_Exon_1 | 5975, 5981, 5983, | 6017, 14291- | 6027, 6036, |
| | 5991, 6003, | 14574 | 14575-14874 |
| | 13935-14290 | | |
| Upstream_Exon_2 | 915, 918, 930, | 962, 965, 972, 988, | 1011, 1014, 1021, |
| | 940, 1071, 1080, | 1113, 1124, 6555, | 1025, 1157, 1168, |
| | 6474, 6479, 6481, | 6560, 6562, 6568, | 6634, 6640, 6642, |
| | 6487, 6492, 6494, | 6570, 6574, 6577, | 6648, 6650, 6654, |
| | 6496, 6498, 6506, | 6579, 6587, 6591, | 6656, 6658, 6661, |
| | 6510, 6514, 6517- | 6595, 6598, 6604, | 6663, 6671, 6675, |
| | 6518, 6526, 6528, | 6606, 6608, 6610, | 6679, 6682, 6690, |

TABLE 2-continued

Guide sequences designed for use as described in the embodiments herein. Each engineered
guide molecule is further designed such as to associate with a target genomic DNA
sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| | 6530, 6532, 6536-6537, 6540, 6542, 6544, 6546, 6720, 6725, 6733, 6737, 6742, 6746, 6752, 6754, 6758, 6764, 6767, 14875-15284 | 6614-6615, 6618, 6620, 6622, 6624, 6779, 6784, 6792, 6794, 6799, 6803, 6807, 6810, 6814, 6821, 6824, 15285-15688 | 6692, 6694, 6696, 6700-6701, 6704, 6706, 6708, 6710, 6836, 6841, 6848, 6852, 6858, 6862, 6867, 6870, 6874, 6881, 6884, 15689-16091 |
| Upstream_Exon_3 | 6474, 6479, 6481, 6487, 6492, 6494, 6496, 6498, 6506, 6510, 6514, 6517-6518, 6526, 6528, 6530, 6532, 6536-6537, 6540, 6542, 6544, 6546, 6720, 6725, 6733, 6737, 6742, 6746, 6752, 6754, 6758, 6764, 6767, 14875-14876, 14879, 14884, 14889, 14891, 14896, 14899, 14901, 14908, 14910-14913, 14916, 14922, 14924-14926, 14930, 14932-14933, | 6555, 6560, 6562, 6568, 6570, 6574, 6577, 6579, 6587, 6591, 6595, 6598, 6604, 6606, 6608, 6610, 6614-6615, 6618, 6620, 6622, 6624, 6779, 6784, 6792, 6794, 6799, 6803, 6807, 6810, 6814, 6821, 6824, 15285-15286, 15289, 15294, 15298, 15300, 15305, 15308, 15310, 15317, 15319-15322, 15325, 15331, 15333-15335, 15339, 15341-15342, 15344, | 6634, 6640, 6642, 6648, 6650, 6654, 6656, 6658, 6661, 6663, 6671, 6675, 6679, 6682, 6690, 6692, 6694, 6696, 6700-6701, 6704, 6706, 6708, 6710, 6836, 6841, 6848, 6852, 6858, 6862, 6867, 6870, 6874, 6881, 6884, 15689-15690, 15693, 15698, 15702, 15704, 15709, 15712, 15714, 15721, 15723-15726, 15729, 15735, 15737-15739, 15743, 15745- |
| Upstream_Exon_3 | 14935, 14940-14942, 14948-14950, 14953, 14955-14956, 14961, 14963, 14967-14970, 14972-14973, 14975, 14979, 14986, 14988, 14992, 14994, 14999, 15001-15002, 15004, 15007, 15010, 15012-15014, 15018-15022, 15029, 15035-15040, 15043, 15048, 15052-15053, 15055, 15061-15064, 15066, 15072, 15075, 15079-15081, 15084, 15088-15089, 15091, 15095, 15097, 15101-15103, 15107, 15109-15111, 15114, 15116-15118, 15121, 15125, 15129, 15133, 15138, 15141, 15144, 15148, 15150-15151, 15155-15156, 15158, 15164, 15168-15170, 15175-15176, 15178-15180, 15182-15183, 15186-15187, 15190, 15193-15196, 15200, 15202- | 15349-15351, 15357-15358, 15361, 15363-15364, 15369, 15371, 15374-15377, 15379-15380, 15382, 15386, 15393, 15395, 15399, 15401, 15406, 15408-15409, 15411, 15414, 15417, 15419-15421, 15425-15429, 15440-15445, 15448, 15453, 15457-15458, 15460, 15466-15470, 15476, 15479, 15483-15485, 15488, 15492-15493, 15495, 15499, 15501, 15505-15507, 15511, 15513-15515, 15518, 15520-15522, 15525, 15529, 15533, 15537, 15542, 15545, 15548, 15552, 15554-15555, 15559-15560, 15562, 15568, 15572-15574, 15579-15580, 15582, 15584-15585, 15587-15588, 15591-15592, 15595, 15598-15601, 15604, 15606-15607, 15609, | 15746, 15748, 15753-15755, 15761-15762, 15765, 15767, 15772, 15774, 15778-15781, 15783-15784, 15786, 15790, 15797, 15799, 15803, 15805, 15810, 15812-15813, 15815, 15818, 15821, 15823-15825, 15829-15833, 15844-15849, 15852, 15857, 15862-15863, 15865, 15871-15875, 15881, 15884, 15888-15890, 15896-15897, 15899, 15903, 15905, 15909-15911, 15914, 15916-15918, 15921, 15923-15925, 15928, 15932, 15936, 15940, 15945, 15948, 15951, 15955, 15957-15958, 15962-15963, 15965, 15971, 15975-15977, 15982-15983, 15985, 15987-15988, 15990-15991, 15994-15995, 15998, 16001-16004, 16007, 16009-16010, 16012, |

TABLE 2-continued

Guide sequences designed for use as described in the embodiments herein. Each engineered
guide molecule is further designed such as to associate with a target genomic DNA
sequence of interest that lies next to a protospacer adjacent motif (PAM).

| Target | SEQ ID NOs of 20 base guides | SEQ ID NOs of 21 base guides | SEQ ID NOs of 22 base guides |
|---|---|---|---|
| Upstream_Exon_3 | 15203, 15205, 15208-15209, 15214, 15216, 15219, 15222-15223, 15227, 15231, 15233, 15235-15237, 15239-15240, 15243-15244, 15248-15252, 15254-15256, 15259, 15262-15264, 15266, 15268-15269, 15271, 15273-15277, 15279-15280, 15282-15284, 16092-16329 | 15612-15613, 15618, 15620, 15623, 15626-15627, 15631, 15635, 15637, 15639-15641, 15643-15644, 15647-15648, 15652-15656, 15658-15660, 15663, 15666-15668, 15670, 15672-15673, 15675, 15677-15681, 15683-15684, 15686-15688, 16330-16559 | 16015-16016, 16021, 16023, 16026, 16029-16030, 16034, 16038, 16040, 16042-16044, 16046-16047, 16050-16051, 16055-16059, 16062-16064, 16067, 16069-16071, 16073, 16075-16076, 16078, 16080-16084, 16086-16087, 16089-16091, 16560-16791 |
| Upstream_Exon_4 | 2905, 6043, 6046, 6049, 6051, 6058, 6074, 6077, 6082-6087, 6089, 16792-17211 | 2950, 6096, 6100, 6103, 6105, 6111, 6127, 6131, 6136-6141, 6143, 17212-17613 | 3032, 6150, 6153, 6156, 6159, 6166, 6182, 6186, 6192-6197, 6200, 17614-18021 |
| Upstream_Exon_5 | 6205, 6208, 6210, 6221, 6223, 6225, 6232, 6234, 6236, 6239-6240, 6242, 6244, 6246, 6255, 6261, 6263, 6273, 6275, 6282, 6284, 6286-6287, 6892, 6899, 6905, 6909, 6913, 6918-6919, 6923, 6927, 6929, 6934, 6936, 6938, 6940, 6945, 6947, 6951, 6960-6961, 6964, 6970-6972, 18022-18425 | 6289, 6292, 6294, 6305, 6307, 6309, 6317, 6319, 6321, 6323, 6325, 6327, 6329, 6331, 6333, 6342, 6349, 6351, 6361, 6363, 6370, 6372, 6374-6375, 6976, 6983, 6989, 6993, 6997, 7004-7006, 7010, 7014, 7016, 7021, 7023, 7025, 7027, 7032, 7034, 7038, 7047, 7049, 7052, 7058-7060, 18426-18822 | 6377, 6380, 6382, 6394, 6397, 6399, 6407, 6409, 6411, 6413, 6415, 6417, 6419-6420, 6422, 6424, 6433, 6441, 6443, 6453, 6455, 6462, 6464, 6466-6467, 7064, 7071, 7077, 7082, 7086, 7093-7095, 7099, 7103, 7105, 7111-7112, 7114, 7116, 7118, 7123, 7125, 7129, 7138, 7140, 7143, 7150-7152, 18823-19217 |
| Upstream_Exon_6 | 7162, 7164, 7170, 7175, 7180, 7184-7185, 7187, 7190, 7192, 7195, 7198, 7204, 7206, 7209-7210, 7214, 7216, 7222, 7224, 7226, 7230, 7235, 11629, 19218-19515, 19515-19638 | 7246, 7248, 7254, 7259, 7264, 7269, 7271, 7273, 7276, 7278, 7281, 7284, 7290, 7292, 7295-7296, 7300, 7302, 7308, 7310, 7312, 7316, 7318, 7322, 19639-20049 | 7334, 7336, 7342, 7348, 7353, 7359, 7361, 7363, 7366, 7368, 7371, 7373, 7375, 7381, 7383, 7386, 7388, 7392, 7394, 7400, 7402, 7404, 7408, 7410, |
| Upstream_Exon_6 | | | 7414, 20050-20465 |

The SNP ID NOs indicated in Table 2 are based on NCBI's 2018 database of Single Nucleotide Polymorphisms (dbSNP). For variants/mutations with no available rs number, variant/mutation characteristics are indicated based on gnomAD v3 database and UCSC Genome Browser assembly ID: hg38, sequencing/assembly provider ID: Genome reference consortium Human GRCh38.p12 (GCA_00001405.27) Assembly date December 2013 initial release December 2017 patch release 12).

For the foregoing embodiments, each embodiment disclosed herein is contemplated as being applicable to each of the other disclosed embodiments. For example, it is understood that any of the RNA molecules or compositions of the present invention may be utilized in any of the methods of the present invention.

EXPERIMENTAL DETAILS

Example 1: RPS19 Correction Analysis

Guide sequences comprising 17-22 contiguous nucleotides containing nucleotides in the sequence set forth in any one of SEQ ID NOs 1-20465 are screened for high on target activity. On target activity is determined by DNA capillary electrophoresis analysis.

According to DNA capillary electrophoresis analysis, guide sequences comprising 17-22 contiguous nucleotides containing nucleotides in the sequence set forth in any one of SEQ ID NOs 1-20465 are found to be suitable for correction of the RPS19 gene. In some embodiments, the guide sequences are suitable for specific, on target activity against only a RPS19 mutant allele. In additional embodiments, the guide sequences are suitable for non-discriminatory targeting to any RPS19 allele.

Example 2: RPS19 Guide Activity Test

Figure 2:
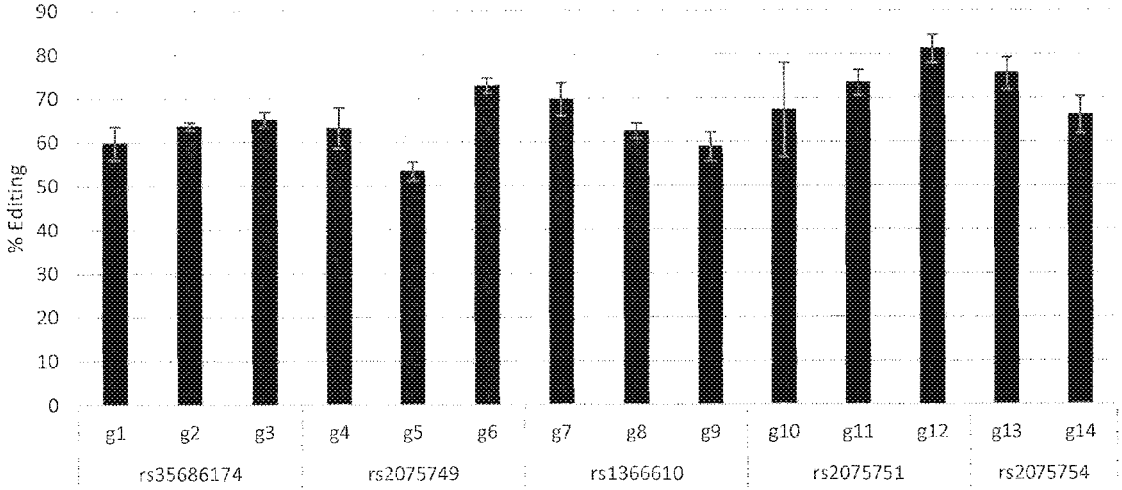
FIG. 2: Screen for activity of guides targeting RPS19 in Hela cells. A spCas9 coding plasmid was co-transfected with each of the guide DNA plasmids. Cells were harvested 72 h post DNA transfection. Genomic DNA was extracted and used for IDAA using on-target primers which amplify the endogenous genomic regions. The graph represents the average % editing (±standard deviation) of three independent experiments. The guides shown in FIG. 2 correspond to the sequence listing as follows: g1 (SEQ ID NO: 6496), g2 (SEQ ID NO: 6479), g3 (SEQ ID NO: 6539), g4 (SEQ ID NO: 6544), g5 (SEQ ID NO: 6471), g6 (SEQ ID NO: 6482), g7 (SEQ ID NO: 6053), g8 (SEQ ID NO: 6075), g9 (SEQ ID NO: 6047), g10 (SEQ ID NO: 6212), g11 (SEQ ID NO: 6275), g12 (SEQ ID NO: 6268), g13 (SEQ ID NO: 7199), and g14 (SEQ ID NO: 7160).

To choose the optimal guides for editing strategies in RPS19-mediated DBA indication, 14 different DNA guides, which are targeting SNPs in different areas of RPS19 relevant to the therapeutic editing strategies, were screened for high on target activity in HeLa cells, which are homozygous to the reference allele. Briefly, spCas9 coding plasmid (64 ng) was co-transfected with each of the guide DNA plasmids (20 ng) in 96 well plate format using jetOPTIMUS reagent (Polyplus). Cells were harvested 72 h post DNA transfection. Genomic DNA was extracted and used for Indel Detection by Amplicon Analysis (IDAA) using on-target primers which amplify the endogenous genomic regions. The graph in FIG. 2 represents the average % editing (±standard deviation) of three independent experiments. According to capillary electrophoreses analysis, all guides show activity ranging between 50%-80%.

---

SEQUENCE LISTING

The patent contains a lengthy sequence listing. A copy of the sequence listing is available in electronic form from the USPTO web site (https://seqdata.uspto.gov/docdetail?docId=US12698513B2). An electronic copy of the sequence listing will also be available from the USPTO upon request and payment of the fee set forth in 37 CFR 1.19(b)(3).

---

The invention claimed is:

1. An isolated guide RNA molecule (gRNA) that targets a mutant Ribosomal Protein S19 (RPS19) allele, wherein the gRNA comprises a CRISPR RNA (crRNA) molecule comprising the nucleic acid sequence set forth in SEQ ID NOs: 6269, 6357, 6449, 6315, 6405, or 6388.

2. The isolated gRNA of claim 1, wherein the crRNA molecule comprises the nucleic acid sequence set forth in SEQ ID NO: 6269.

3. An isolated gRNA that targets a mutant RPS19 allele, wherein the gRNA comprises a crRNA molecule consisting of the nucleic acid sequence set forth in SEQ ID NO: 6269, 6357, 6449, 6315, 6405, or 6388.

4. The isolated gRNA of claim 3, wherein the crRNA molecule consists of the nucleic acid sequence set forth in SEQ ID NO: 6269.

5. The isolated gRNA of claim 3, wherein the crRNA molecule consists of the nucleic acid sequence set forth in SEQ ID NO: 6357.

6. The isolated gRNA of claim 3, wherein the crRNA molecule consists of the nucleic acid sequence set forth in SEQ ID NO: 6449.

7. The isolated gRNA of claim 3, wherein the crRNA molecule consists of the nucleic acid sequence set forth in SEQ ID NO: 6315.

8. The isolated gRNA of claim 3, wherein the crRNA molecule consists of the nucleic acid sequence set forth in SEQ ID NO: 6405.

9. The isolated gRNA of claim 3, wherein the gRNA comprises a crRNA consisting of the nucleic acid sequence set forth in SEQ ID NO: 6388.

10. A composition comprising the isolated guide RNA molecule of claim 1, a donor DNA template for homology directed repair (HDR), alteration, or replacement of a target sequence of the RPS19 allele, one or more CRISPR nucleases or sequences encoding the one or more CRISPR nucleases, and one or more tracrRNA molecules or sequences encoding the one or more tracrRNA molecules.

* * * * *